US010851350B1

(12) United States Patent
Cappello et al.

(10) Patent No.: US 10,851,350 B1
(45) Date of Patent: Dec. 1, 2020

(54) BIOREACTOR PRODUCTION OF VIRUS FROM ADHERENT CELLS

(71) Applicant: Genelux Corporation, San Diego, CA (US)

(72) Inventors: Joseph Cappello, San Diego, CA (US); Richard J. Aguilar, San Diego, CA (US)

(73) Assignee: Genelux Corporation, San Diego, CA (US)

(*) Notice: Subject to any disclaimer, the term of this patent is extended or adjusted under 35 U.S.C. 154(b) by 6 days.

(21) Appl. No.: 16/020,850

(22) Filed: Jun. 27, 2018

Related U.S. Application Data

(60) Provisional application No. 62/525,734, filed on Jun. 27, 2017.

(51) Int. Cl.
C12N 15/86 (2006.01)
A61K 38/21 (2006.01)
C07K 14/56 (2006.01)
C12N 7/02 (2006.01)
C12N 5/077 (2010.01)

(52) U.S. Cl.
CPC .............. C12N 7/02 (2013.01); C12N 5/0656 (2013.01); C12N 2710/10051 (2013.01); C12N 2710/16051 (2013.01); C12N 2710/24151 (2013.01); C12N 2760/20251 (2013.01)

(58) Field of Classification Search
None
See application file for complete search history.

(56) References Cited

U.S. PATENT DOCUMENTS

| | | | |
|---|---|---|---|
| 5,976,796 A | 11/1999 | Szalay et al. | 435/6 |
| 7,588,767 B2 | 9/2009 | Szalay et al. | 424/199.1 |
| 7,754,221 B2 | 7/2010 | Szalay et al. | 424/199.1 |
| 7,901,921 B2 * | 3/2011 | Coffey | C12N 7/00 424/215.1 |
| 8,323,959 B2 | 12/2012 | Szalay et al. | 435/320.1 |
| 8,597,939 B2 | 12/2013 | Castillo Fernandez | 435/297.2 |
| 8,857,927 B2 | 10/2014 | Johnson et al. | 312/301 |
| 8,986,979 B2 | 3/2015 | Castillo et al. | 435/287.1 |
| 9,005,602 B2 | 4/2015 | Szalay et al. | 424/93.3 |
| 2012/0308484 A1 | 12/2012 | Szalay et al. | 424/9.3 |
| 2016/0339066 A1 | 11/2016 | Szalay et al. | 424/133.1 |
| 2017/0051309 A1 | 2/2017 | Lesch et al. | 424/93.21 |

FOREIGN PATENT DOCUMENTS

| | | |
|---|---|---|
| WO | WO 2007/059473 | 5/2007 |
| WO | WO 2016/048556 | 3/2016 |

OTHER PUBLICATIONS

Pugalenthi et al. (Cancer Gene Therapy, 2015, p. 591-596).*

Letter/Written Disclosure of the Information Disclosure Statement for the above-referenced application, filed herewith on Aug. 14, 2018, 2 pages.
Agranovski et al., "Rapid detection of airborne viruses by personal bioaerosol sampler combined with the PCR device," Atmospheric Environment 40:3924-3929 (2006).
Al'tshtein et al., "Isolation of a recombinant vaccinia virus based on the LIVP strain inducing a surface antigen of the hepatitis B virus," Dokl. Akad. Nauk. SSSR 285(3):696-699 (1985) [Article in Russian].
ATCC Accession No. VR-1549, Product Sheet, Retrieved on Aug. 9, 2018 from: <URL:atcc.org/Products/All/VR-1549.aspx#documentation, 2 pages.
Berthet, P., "Virus Production with the iCELLis® Single-Use Bioreactor," Poster P088, European Society of Gene and Cell Therapy (ESGCT) meeting, The Hague, The Netherlands, Oct. 23-26, 2014, 4 pages.
Certified English translation of Al'tshtein [Altshteyn] et al., "Isolation of a recombinant vaccinia virus based on the LIVP strain inducing a surface antigen of the hepatitis B virus," Dokl. Akad. Nauk. SSSR. 285(3):696-699 (1985).
Chkheidze et al., "Identification of DNA binding proteins in vaccinia virus by DNA-protein crosslinking," FEBS 336(2):340-342 (1993).
Franke et al., "Genetic engineering, production and characterisation of monomeric variants of the dimeric *Serratia marcescens* endonuclease," FEBS Letters 425: 517-522 (1998).
Illingworth et al., "Adeno-Associated Virus Production Using a Disposable Fixed-Bed Bioreactor From Bench-Scale to Industrial Scale," Abstract 89, Mol. Ther. 22(Suppl 1):S33 (2014).
Illingworth et al., "Adeno-Associated Virus Production Using a Disposable, Fixed-Bed Bioreactor: From Bench Scale to Industrial Scale," Poster, European Society of Gene and Cell Therapy (ESGCT) meeting, The Hague, The Netherlands, Oct. 23-26, 2014, 2 pages.
Karhinen et al., "Consistent Viral Vector Manufacturing for Phase III Using iCELLis 500 Fixed-Bed Technology," Abstract 706, Mol. Ther. 24(Suppl 1):S279 (2016).
Kozlova et al., "Inactivation and Mineralization of Aerosol Deposited Model Pathogenic Microorganisms over $TiO_2$ and $Pt/TiO_2$," Environ. Sci. Technol. 44:5121-5126 (2010).
Kutinova et al., "Hepatitis B virus proteins expressed by recombinant vaccinia viruses: influence of preS2 sequence on expression surface and nucleocapsid proteins in human diploid cells," Arch. Virol. 134:1-15 (1994).
Kutinova et al., "Search for optimal parent for recombinant vaccinia virus vaccines. Study of three vaccinia virus vaccinal strains and several virus lines derived from them," Vaccine 13(5): 487-493 (1995).

(Continued)

Primary Examiner — Agnieszka Boesen
(74) Attorney, Agent, or Firm — Dentons US LLP; Stephanie Seidman

(57) ABSTRACT

Methods for producing viruses from adherent cells are provided. The methods include releasing virus from adherent host cells grown in a bioreactor, and purifying released virus by ultrafiltration and/or diafiltration. The methods can be used to manufacture viruses, including for clinical use, at reduced cost relative to conventional virus manufacturing methods.

49 Claims, 20 Drawing Sheets
(19 of 20 Drawing Sheet(s) Filed in Color)

(56) References Cited

OTHER PUBLICATIONS

Lefebvre et al., "Development of a Scalable Viral Vector Upstream Process for Gene Therapy: rAAV-8 Production by Transient Transfection of HEK-293 Cells in iCELLis® Bioreactor," Poster, European Society of Gene and Cell Therapy (ESGCT) meeting, Berlin, Germany, Oct. 17-20, 2017, 1 page.

Lesch et al., "Process Development of Adenoviral Vector Production in Fixed Bed Bioreactor: From Bench to Commercial Scale," Human Gene Therapy 26(8):560-571 (2015).

Shchelkunov et al., "The gene encoding the late nonstructural 36K protein of vaccinia virus is essential for virus reproduction," Virus Res. 28: 273-283 (1993).

Sroller et al., "Effect of 3-beta-hydroxysteroid dehydrogenase gene deletion on virulence and immunogenicity of different vaccinia viruses and their recombinants," Arch. Virol. 143:1311-1320 (1998).

Van der Loo, J.C.M. and J.F. Wright, "Progress and challenges in viral vector manufacturing," Hum. Mol. Gen. 25(R1):R42-R52 (2016).

Zinoviev et al., "Identification of the gene encoding vaccinia virus immunodominant protein p35," Gene 147: 209-214 (1994).

Letter/Written Disclosure of the Information Disclosure Statement for the above-referenced application, filed herewith on Oct. 6, 2020, 2 pages.

Rescission of Previous Nonpublication Request (35 U.S.C. 122(b)(2)(B)(ii)), and Notice of Foreign Filing (35 U.S.C. 122(b)(2)(B)(iii)), filed Oct. 1, 2020, in connection with U.S. Appl. No. 16/020,850, 3 pages.

\* cited by examiner

ATMI iCellis Nano Bioreactor and Control/Data Management System

Micrographic images of crystal violet stained carriers of iCellis Nano bioreactor Experiment 6.

Pre-Seeding                                    Pre-Seeding iCellis Nano CV-1 Cell Culture Carrier Images (Crystal Violet)

Post-seeding                                   Post-Seeding

CV-1 growth profile and virus amplification of iCellis Experiment 1 and roller bottle controls. Vertical line indicates time of infection.

CV-1 growth profile and virus amplification of iCellis Experiment 2 and roller bottle controls. Vertical line indicates time of infection.

CV-1 growth profile and virus amplification of iCellis Experiment 3 and roller bottle controls. Vertical line indicates time of infection.

CV-1 growth profile and virus amplification of iCellis Experiment 4 and roller bottle controls. Vertical line indicates time of infection.

CV-1 growth profile and virus amplification of iCellis Experiment 5 and roller bottle controls. Vertical line indicates time of infection.

CV-1 growth profile and virus amplification of iCellis Experiment 6 and roller bottle controls. Vertical line indicates time of infection.

Individual growth curves of iCellis Nano Experiments 2 to 6. Data was fit to linear equations to show relative trends.

Compiled growth data of CV-1 cells in iCellis Bioreactor Experiments 2 to 6 throughout the growth phase. The data was fit to an exponential equation. The calculated population doubling time was 140 hours.

Compiled growth data of CV-1 cells in iCellis Bioreactor Experiments 2 to 6 to 150 hours of the growth phase. The data was fit to an exponential equation. The calculated population doubling time was 99 hours.

Compiled cell density data of CV-1 cells in roller bottle controls of Experiments 1 to 6 through 300 hours of the growth phase. The data was fit to an exponential equation. The calculated population doubling time was 105 hours.

Compiled cell density data of CV-1 cells in roller bottle controls of Experiments 1 to 6 through 150 hours of the growth phase. The data was fit to an exponential equation. The calculated population doubling time was 118 hours.

Individual growth curves of iCellis Nano Experiments 1 and 3-6 after infection with GLV-1h68. Data was fit to exponential equations.

Virus amplification data from Nano Experiments 1 and 3-6. Data was fit to $2^{nd}$ order polynomial equations, except for Experiment 6 which was best fit by a linear equation.

CV-1 growth profile of iCellis Experiments 7, 8 and 9. Vertical lines indicate
the time points in each bioreactor experiment at which infection was
initiated with GLV-1h68. The data was plotted in hours post-seeding to allow
calculation of the PDT in hours.

Evaluation of virus extraction conditions from bioreactor carriers (Trial 4).

Evaluation of virus stability in TrypLE (Trial 8).

BIOREACTOR PRODUCTION OF VIRUS FROM ADHERENT CELLS

RELATED APPLICATIONS

Benefit of priority is claimed to U.S. provisional application Ser. No. 62/525,734, filed Jun. 27, 2017, inventors Joseph Cappello and Richard J. Aguilar, entitled "Bioreactor Production of Virus from Adherent Cells." The subject matter of this application is incorporated by reference in its entirety.

FIELD OF THE INVENTION

Provided are methods for virus production from adherent cells.

BACKGROUND

Viruses are used as therapeutics. Among such uses are as vaccines, gene therapy vectors and virotherapy agents. The manufacture of viruses for these purposes involves the replication of virus in suitable host cells, and then purification of the virus from the host cells. Host cells used for replication of viruses are either grown in anchorage-dependent, adherent culture conditions or in suspension culture conditions. An advantage of the suspension culture is that the cells can be cultured in a single bioreactor in large volume. Some viruses, however, do not replicate well in suspension-cultured cells.

Anchorage-dependent cells, in which viruses replicate well, are commonly cultured in roller bottles, which require a large number of bottles to obtain sufficient amounts. These processes, thus, are difficult and expensive to scale. In either case, whether using adherent or suspension culture conditions, the virus infected cells are harvested from the culture vessel or vessels, either the bioreactor or the roller bottles, and lysed to release the virus. The virus is purified from the total host cell-derived components using numerous and various steps including several or more of homogenization, sonication, centrifugation, filtration, affinity purification, chromatography, and density gradient ultracentrifugation. The culture conditions and the purification steps involved in the manufacture of viruses add complication and cost to the manufacturing processes, and can result in low yields. Hence, simpler and scalable methods for manufacturing viruses are needed.

SUMMARY

Provided are simplified scalable methods for the manufacture of viruses in high yield. The methods employ virus-infected anchorage-dependent cells. In accord with the methods, the virus is released from the host cells while the host cell components remain substantially attached to the culture surface. Host cell-derived components remain with cells remnants, while the virus is released into the cell culture medium, and the virus is purified by a simplified, cost-effective single step process of ultrafiltration or diafiltration or a two-step process of ultrafiltration and diafiltration. The purification process is high yield, and can be performed in a day or less. The process can be performed with cells grown in a bioreactor that is suitable for culturing anchorage-dependent cells, thereby combining the simplified purification methods with the advantages of bioreactor scale-up. Any virus, particularly enveloped viruses, which can infect and grow in cells that can be grown in an adherent format can be manufactured by these methods.

Among the methods/processes are those for producing viruses from adherent cells cultured in bioreactors. The methods involve releasing the virus from adherent host cells in a bioreactor, and purifying the released virus by ultrafiltration and/or diafiltration. Described herein are various examples and aspects of such methods.

Provided are methods (processes) for producing a virus. The methods include the steps of: a) culturing host cells, comprising a virus, in a bioreactor, wherein the bioreactor comprises a matrix for growing adherent cells or cells entrapped therein, wherein the matrix is biocompatible; the cells are entrapped in and/or adhere to the matrix; and the density of the matrix is such that the cells remain attached under conditions in which cells are lysed and treated to release the virus, and the flow of cell culture medium through the matrix is sufficient for cell growth; b) treating the cells to lyse them and release the virus into the medium in the bioreactor; and then c) without further treatment, and in only one or only two steps, purifying the released virus from the cell culture medium. The one step is ultrafiltration or diafiltration; and the two steps are ultrafiltration and diafiltration. No other purification steps are employed. Thus, purification after lysing and releasing the virus from the cells, is effected only by ultrafiltration and/or diafiltration. Purification is achieved in only the one or the two steps. The purification can be effected in 1 day or less.

The bioreactor contains a matrix or surface onto which adherent cells attach, and suspension cells can be entrapped. The matrix (or macrocarrier or substrate or surface) can be a non-fixed attachment surface. The matrix or surface can be selected from among, but not limited to microcarrier beads, fibers, or woven mesh in suspension. The matrix or surface can be a fixed attachment surface. The bioreactor can be, for example, a packed bed bioreactor. Other configurations can be selected by the skilled artisan, as long as the bioreactor contains a matrix or surface for retaining the cells during growth and lysis.

The host cells are cells that adhere to the matrix or that are entrapped in the matrix, including cells that normally grow in suspension, so that upon processing the cells and medium, the cells are not released. In general, the host cells are adherent cells. The cells can be primary cells, or cell lines. The particular cells are those suitable for growing a particular virus. Among the cell lines are known cell lines, such as CV-1 cells, KB cells, Vero cells, CHO cells and others. Cells include, but are not limited to, mammalian cells, including human and other primate cells; human cells include, for example, human fibroblast cells, epithelial cells and endothelial cells.

As exemplified herein, the exemplified cells are CV-1 cells, and the virus is a vaccinia virus, such as a therapeutic vaccinia virus. Prior to purification, the cell process medium can be harvested. Optionally, the medium can be stored. The methods for producing the virus can include only steps a), b) and c), above, or can include additional steps prior to purification, which only includes the one or two steps of ultrafiltration and/or diafiltration.

Releasing of the virus includes treatments, such as freeze/thaw and/or treatment with hypotonic medium and/or treatment with detergent, to lyse the cells. The virus is released into the medium from lysed cells by treatment with a protease and/or nuclease. The protease generally is a non-specific protease, such as a digestive enzyme, such as trypsin. The nuclease is a DNase or RNase, such as the endonuclease from *Serratia marcescens*, sold under the trademark Benzonase®. Treatment with nuclease is optional. The lysis and enzyme treatments can be performed sequentially or together. Lysis should precede or be conducted with the protease or nuclease treatment. The protease and nuclease treatments can be effected together or in any order.

The virus can be any virus of interest, such as therapeutic viruses, including oncolytic viruses, and vaccines, and gene therapy vectors, and viruses for delivery of gene products. Generally, since purification is effected with released virus, and release can include nuclease treatment, the viruses are enveloped viruses. Viruses include, but are not limited to, poxviruses, such as a vaccinia virus, myxoma virus, measles virus, reovirus, vesicular stomatitis virus (VSV), adenoviruses, adeno-associated virus, poliovirus, herpes viruses, Sindbis virus and Seneca Valley virus, ora derivative thereof that is modified to contain nucleic acid encoding a heterologous gene product. The virus can be an oncolytic virus, such as vaccinia viruses (e.g., GL-ONC1, Pexa-Vec, vvDD, JX-929, and WO-12), vesicular stomatitis viruses (e.g., VSV-IFNbeta-NIS, VSV-E6/7, VSV-GFP), measles viruses (e.g., MV-NIS, MV-Edm, MV-NPL), seneca valley viruses (e.g., SVV-001 and NTX-010), reovirus (e.g., Reolysin), adenoviruses (e.g., CGTG-102, Oncos-102, NG-348, NG-350, NG-347, NGaFAB, NG-aEpCAM, ONYX-015, CG7870, VCN-01, LOAd703, Ad5, Ad3/5, CRAd-CXCR4-5/3, OvAdl, dI1520), parvovirus (e.g., H1-PV), marabaviruses (e.g., MG1MA3, MG1-HPV, and MB1-Neoantigen), new castle disease virus (e.g., NDV-HUJ), retrovirus (e.g., Toca511), coxsackievirus (e.g., CAVATAK), and herpes viruses (e.g., HSV-1716, NV1020, Imlygic (T-Vec), ONCR-1/-2, and HSV-1716). The viruses can be attenuated and/or modified. Oncolytic vaccinia viruses include, but are not limited to, Lister, such as LIVP strains and clonal strains thereof, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 NYVAC strain, and the modified Wyeth strain, JX-594. Exemplary of oncolytic LIVP strains of virus is the strain designated GLV-1h68 (also referred to as GL-ONC1). Included among the viruses are modified viruses that encoded a heterologous gene product(s), including therapeutic products, and reporter genes and other detectable markers.

The virus is purified by ultrafiltration and/or diafiltration. The skilled person can select the appropriate form of membrane and mode of ultrafiltration. For example, ultrafiltration can employ, for example a membrane having a nominal molecular weight cut off of between 300 and 750 kilodaltons or a nominal porosity of between 0.05 and 0.2 μm. It can employ a membrane that contains polyethersulfone. The member can be flat, or can be a hollow fiber membrane. The ultrafiltration can be performed in a tangential flow mode, in a cross flow mode, or other mode selected by the skilled artisan. Ultrafiltration can be followed by diafiltration, or diafiltration can be performed without ultrafiltration. Recovery of the processed released virus is greater than 50%, and can be as high as 90%, 95% or more.

BRIEF DESCRIPTION OF THE DRAWINGS

This application includes at least one drawing executed in color. Copies of any patent or any publication, based on this application, with color drawing(s), will be provided by the Office upon request and payment of the requisite fee.

Figure 1:
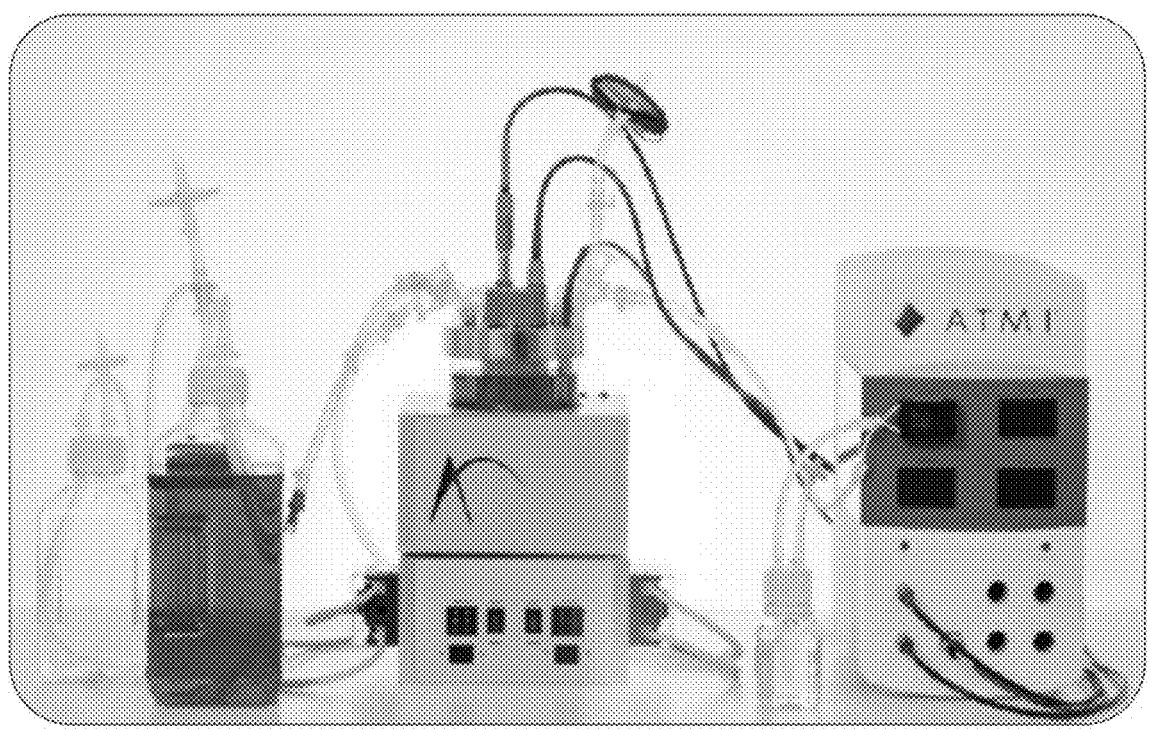
FIG. 1 shows an exemplary bioreactor, the ATMI iCellis® Nano Bioreactor and Control/Data Management System.

The above-identified figures are provided by way of representation and not limitation.

Outline
- A. Definitions
- B. Overview. C. Bioreactor and matrix
- D. Cells and growth
- E. Virus and inoculation
- F. Cell Lysis and release of virus into the process medium
- G. Diafiltration and ultrafiltration of the process medium to purify virus
- H. Examples

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, Genbank® sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the Internet can come and go, but equivalent information can be found by searching the internet. Reference thereto evidences the availability and public dissemination of such information.

As used herein, a bioreactor refers to a cell culture device. For use in the methods herein the bioreactor contains a matrix for culturing adherent cells. The matrix is one that retains the cells, such that they are not released into the cell culture medium when lysed. An exemplary bioreactor are those sold under the trademark iCellis® bioreactor. This bioreactor was developed by ATMI Life Sciences and is available from PALL Biosciences.

As used herein, "carrier" or alternatively "substrate" refers to any solid-state material that provides a biocompatible surface onto which adherent cells adhere in culture.

As used herein, matrix type carriers contain polyester fibers, optionally held within a cage (for example, of polypropylene) to immobilize the fibers.

As used herein, process medium refers to the medium in the bioreactor in which the cells are cultured, and virus produced, and the medium used in processing the cells and producing the virus.

As used herein, large-scale manufacture is defined by the single patient dose, and the annual demand for doses. It varies for the virus and treatment; but each large-scale preparation provides about 1/6 to 1/12, such as about 1/10 of the number yearly doses. Hence, for example, for the vaccinia virus, designated GLV-1h68 (GL-ONC1), large scale manufacturing provides an annual production of about 10,000 treatments at a dose of about $6 \times 10^9$ plaque forming units (pfu) per treatment dose or $6 \times 10^{13}$ total annual pfu. Assuming 8-12, such as 10 production batches per year, each large scale batch should produce 1,000 treatment doses or about $10^{11}$ to $10^{13}$, such as about $5\text{-}6 \times 10^{12}$ pfu. Exemplary pfu and doses of the exemplary virus GLV1h-68 (GLV-ONC1):

| Titer (pfu/ml) | Doses @ $5 \times 10^9$ pfu/dose |
|---|---|
| $6 \times 10^7$ | 12 |
| $8.6 \times 10^8$ | 35 |

-continued

| Titer (pfu/ml) | Doses @ $5 \times 10^9$ pfu/dose |
|---|---|
| $1.2 \times 10^8$ | 80 |
| $2.8 \times 10^8$ | 45 |
| $1.7 \times 10^8$ | 29 |
| $1.1 \times 10^8$ | 108 |

As used herein, "virus titer" or "viral titer" refers to the concentration of a virus and is a given number of infectious virus units per volume, such as plaque forming units (pfu)/mL. Virus titer can be determined by serial dilution of a sample for infection of target cells in order to quantify the number of infectious or active virus in a sample. For example, virus titer can be determined using a plaque assay.

As used herein, a "virus" or virus vector refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. As used herein, oncolytic viruses refer to viruses that replicate selectively in tumor cells in tumorous subjects. Some oncolytic viruses can kill a tumor cell following infection of the tumor cell. For example, an oncolytic virus can cause death of the tumor cell by lysing the tumor cell or inducing cell death of the tumor cell.

As used herein, a therapeutic virus, such as a therapeutic oncolytic virus, is a virus that is used to treat disease or condition. Typically they are not pathogenic or have been rendered non-pathogenic.

As used herein the term "vaccinia virus" or "VACV" or "VV" denotes a large, complex, enveloped virus belonging to the poxvirus family. It has a linear, double-stranded DNA genome approximately 190 kb pairs in length, and which encodes approximately 200 proteins. Vaccinia virus strains include, but are not limited to, strains of, derived from, or modified forms of Western Reserve (WR), Copenhagen, Tashkent, Tian Tan, Lister, Wyeth, IHD-J, and IHD-W, Brighton, Ankara, MVA, Dairen I, LIPV, LC16M8, LC16MO, LIVP, WR 65-16, Connaught, and New York City Board of Health vaccinia virus strains.

As used herein, Lister Strain of the Institute of Viral Preparations (LIVP) or LIVP virus strain refers to a virus strain that is the attenuated Lister strain (ATCC® Catalog No. VR-1549™) that was produced by adaption to calf skin at the Institute of Viral Preparations, Moscow, Russia (Altshteyn et al. (1985) *Dokl. Akad. Nauk USSR* 285:696-699). The LIVP strain can be obtained, for example, from the Institute of Viral Preparations, Moscow, Russia (see. e.g., Kutinova et al. (1995) *Vaccine* 13:487-493); the Microorganism Collection of FSRI SRC VB Vector (Kozlova et al. (2010) *Environ. Sci. Technol.* 44:5121-5126); or can be obtained from the Moscow Ivanovsky Institute of Virology (C0355 K0602; Agranovski et al. (2006) *Atmospheric Environment* 40:3924-3929). It also is well known to those of skill in the art; it was the vaccine strain used for vaccination in the USSR and throughout Asia and India. The strain is well known (see e.g., Altshteyn et al. (1985) *Dokl. Akad. Nauk USSR* 285:696-699; Kutinova et al. (1994) Arch. Virol. 134:1-15; Kutinova et al. (1995) *Vaccine* 13:487-493; Shchelkunov et al. (1993) *Virus Research* 28:273-283; Sroller et al. (1998) *Archives Virology* 143:1311-1320; Zinoviev et al., (1994) *Gene* 147:209-214; and Chkheidze et al. (1993) *FEBS* 336:340-342).

As used herein, LIVP GLV-1h68 (also designated GL-ONC1; see, e.g., U.S. Pat. No. 7,588,767, and US Patent Publication No. US-2016-0339066-A1) is an LIVP virus that contains ruc-gfp (a luciferase and green fluorescent protein fusion gene (see, e.g., U.S. Pat. No. 5,976,796)), beta-galactosidase (LacZ) and beta-glucuronidase (gusA) reporter genes inserted into the F14.5L, J2R (thymidine kinase) and A56R (hemagglutinin) loci, respectively. The genome of GLV-1h68 has a sequence of nucleotides set forth in SEQ ID NO: 3 or a sequence of nucleotides that has at least 97%, 98% or 99% sequence identity to the sequence of nucleotides set forth in SEQ ID NO: 3 of copending published application US-2016-0339066-A1.

As used herein, the term "modified virus" or "recombinant virus," used interchangeably, refers to a virus that is altered compared to a parental strain of the virus. Typically modified viruses have one or more truncations, mutations, insertions or deletions in the genome of virus. A modified virus can have one or more endogenous viral genes modified and/or one or more intergenic regions modified. Exemplary modified viruses can have one or more heterologous nucleic acid sequences inserted into the genome of the virus. Modified viruses can contain one or more heterologous nucleic acid sequences in the form of a gene expression cassette for the expression of a heterologous gene.

As used herein, a modified LIVP virus strain refers to an LIVP virus that has a genome that is not contained in LIVP, but is a virus that is produced by modification of a genome of a strain derived from LIVP. Typically, the genome of the virus is modified by substitution (replacement), insertion (addition) or deletion (truncation) of nucleotides. Modifications can be made using any method known to one of skill in the art such as genetic engineering and recombinant DNA methods. Hence, a modified virus is a virus that is altered in its genome compared to the genome of a parental virus. Exemplary modified viruses have one or more heterologous nucleic acid sequences inserted into the genome of the virus. Typically, the heterologous nucleic acid contains an open reading frame encoding a heterologous protein. For example, modified viruses herein can contain one or more heterologous nucleic acid sequences in the form of a gene expression cassette for the expression of a heterologous gene.

As used herein, when referencing dosage, such as plaque forming units (pfu)/kg, based on mass kg of the subject, an average human subject is considered to have a mass of about 70 kg-75 kg, such as 70 kg.

For clarity of disclosure, and not by way of limitation, the detailed description is divided into the subsections that follow.

B. Overview

Provided are methods/processes that include two stages: a production stage in which the virus is introduced into cells in which it can replicate, and the cells are cultured under conditions in which the virus is produced. The viruses can be enveloped viruses, including but not limited to, poxviruses, such as vaccinia virus. The cells are then lysed to release the virus, and can be treated with an enzyme or enzymes that are nucleases and/or proteases. In the second stage, the process medium is harvested, and the virus is purified only by ultrafiltration or diafiltration or both. Thus, the second stage is only a one or two step process involving only ultrafiltration and/or diafiltration to produce the purified virus.

The processes, thus, include the steps of growing adherent host cells, generally a cell line, in a bioreactor that contains packed biocompatible woven or fibrous matrix material, such as polyester, polyethylene terephthalate. The matrix is of sufficient density to retain by adherence and/or entrapment the cells and also, cellular debris when the cells are lysed.

The host cells are cultured to an appropriate density, and then inoculated with the virus, and cultured to produce the virus. The cells are lysed, such as by freezing and thawing or exposure to hypotonic medium or both, followed by treatment with an enzyme, such as protease, particularly one that cleaves non-specifically, such as trypsin. The cells optionally are treated with a nuclease before, with or after the protease. The lysed cells are retained by the matrix material.

The virus is purified from the medium in only one or two steps, where one step is the ultrafiltration or diafiltration. If two steps are used, they are ultrafiltration and diafiltration. No additional purification steps, other than ultrafiltration and/or diafiltration are employed.

Hence, provided are scalable processes (also referred to as methods) for producing (also referred to as manufacturing) purified viruses, particularly therapeutic viruses, such as oncolytic viruses, vaccines, and gene therapy vectors. Because the methods can be practiced in a bioreactor, the methods are readily scaled up. Purification, which provides high yields of virus, can be effected in one day or less. The resulting virus is produced in high yield, with as much as 95% or more, generally at least 50%, 60%, 70%, 80%, 90% recovery.

C. Bioreactor and Matrix

A bioreactor is a vessel suitable for growing cells and contains a packed matrix substrate of woven or non-woven fibers, fabric or strips of fabric whose fibers or fibrous mesh allow cell attachment (or entrapment) and growth. The matrix can be in a fixed or packed bed or in a fluidized bed.

The bioreactor contains a packed matrix of microcarrier beads, woven or non-woven fibers, fabric or strips of fabric whose fibers or fibrous mesh allow cell attachment and growth. The matrix is such that the cells are not detached or removed from the fabric by enzymatic digestion, such as trypsin digestion. The cells are not detached or removed from the fabric by enzymatic digestion such as trypsin. A hollow fiber bioreactor would not work because cells adherent to the inner surface of the hollow fibers would not be trapped in the matrix and the cells would be able to be detached by enzymatic digestion, such as trypsin. A hollow fiber bioreactor is not contemplated because cells adherent to the inner surface of the hollow fibers would not be trapped in the matrix and the cells can be detached by enzymatic digestion, such as trypsin. In accord with the processes herein, cells that are retained by the matrix, such as anchorage-dependent ("adherent") host cells are grown in the bioreactor; the cells are infected with the virus and grown in the bioreactor on the matrix substrate.

Exemplary of bioreactors, are the bioreactors sold under the trademark iCELLis® (Pall Life Sciences). U.S. Pat. Nos. 8,597,939 and 8,986,979 describe such bioreactors. The iCellis® bioreactor is exemplary of a bioreactor platform that is a scalable line of single-use high cell density bioreactors, allowing small-scale (referred as the "nano" below) to large-scale manufacturing. This bioreactor contains a pre-packed, fixed bed of medical grade polyester microfibers providing a large surface area for growth in a compact bioreactor volume. The main bioreactor is equipped with a built-in magnetic drive impeller that circulates the medium through the fixed bed from the bottom to the top, ensuring low shear stress and high cell viability. At the top of the fixed bed, the medium falls as a thin film down the outer wall where it takes up 02 to maintain dissolved oxygen levels in the bioreactor.

Matrix Materials

Exemplary of matrix materials, are material to which cells can adhere, adherent material, that are biocompatible so that they can be used to culture cells as described herein. Such materials, include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, and an inert metal fiber. Fibers of these materials can be used, in woven or non-woven form. For example in the bioreactor sold under the trademark iCellis®, and used in the working examples herein, the matrix material is polyethylene terephthalate (PET), a polyester. The matrix can be coated with materials that promote cell attachment such as a Matrigel® cell culture substrate, an extra cellular matrix component (e.g., fibronectin, chondronectin, laminin, ProNectin® F), a collagen, or a poly L lactic acid in order to improve its biocompatibility, its cell adherence or its cell retention.

The density of the matrix is sufficient so that the cells and, after lysis, cell debris remain trapped, but is not too high to impede cell medium flow through the matrix and bioreactor, which is necessary for cells to grow. The density of the matrix is such that the cells remain entrapped in the matrix, but the density is not too high to prevent fluid flow throughout the matrix.

The matrix can be a mesh composed of polyester fiber. The diameter of the fiber is typically about 10-40 micrometers. The mesh can be purchased from a textile manufacturer either as bulk fiber, non-woven mesh, or as woven fabric. Some manufacturers produce the fiber specifically for medical purposes and it is qualified for biocompatibility. This medical grade mesh or fabric is of particular utility in that it is compatible with cell attachment and growth in a bioreactor that would be used for biopharmaceutical production.

The density of the packing of such materials is a factor that influences cells remaining trapped in the matrix. The more the fiber density, the greater the filtration effect of the packing, therefore the cells are more likely to remain entrapped in the matrix. The greater packing density, however, is more restrictive to media flow and requires more agitation force to achieve the same media flow. Exemplary densities are about 80-160 g/L, such as 90-150 g/L, such as 96 g/L-144 g/L. This range retains cells, but the greater packing density is more restrictive to media flow and requires more agitation force to achieve the same media flow.

The iCELLis® bioreactor system (see, e.g., FIG. 1) accommodates up to 500 m² of growth area. The projected yields of virus, such as vaccinia virus, for scale-up using 25 L of fixed-bed volume, are as follows:

| Fixed Bed Height | Packing density | iCellis ® Nano (Projected Yield PFU) | iCellis ® 500 (Projected Yield PFU) |
|---|---|---|---|
| 2 cm | 96 g/L | 0.53 m² (3.5 × 10¹⁰) | 67 m² (4.4 × 10¹²) |
|  | 144 g/L | 0.8 m² (5.3 × 10¹⁰) | 100 m² (6.4 × 10¹²) |
| 4 cm | 96 g/L | 1.1 m² (7.3 × 10¹⁰) | 133 m² (8.8 × 10¹²) |
|  | 144 g/L | 1.6 m² (1.1 × 10¹¹) | 200 m² (1.3 × 10¹³) |
| 10 cm | 96 g/L | 2.7 m² (1.8 × 10¹¹) | 334 m² (2.2 × 10¹³) |
|  | 144 g/L | 4.0 m² (2.7 × 10¹¹) | 500 m² (3.3 × 10¹³) |

For the iCellis® bioreactors, two packing densities of PET: 96 g/L and 144 g/L, are exemplified.

D. Cells and Growth

Provided herein are processes (methods) for producing viruses from adherent host cells using the bioreactors. The methods involve releasing the virus from adherent host cells in a bioreactor, and purifying the released virus by one or two steps of ultrafiltration and/or diafiltration. The methods are used to manufacture viruses, including for clinical use, at reduced cost relative to conventional virus manufacturing methods. The purification method, which requires only ultrafiltration and/or diafiltration reduces the time for purification, and provides higher yields of the virus. Purification can be effected in a day or less.

The cells, which are adherent cells, or cells adapted to grow in or on a matrix support, are cultured in a bioreactor. The host cells can be any cells suitable for growing a virus; selection of the cell can depend on the particular virus. Generally, the host cells are adherent cells. The cells include, but are not limited to, mammalian cells of primary origin; transformed or otherwise immortalized cells and cell lines. Exemplary of such cells are: human fibroblast cells; human epithelial cells; and human endothelial cells. Cell lines include, but are not limited to; CV-1 cells; Vero cells; and CHO cells. The cells can be recombinant, and/or genetically modified.

Cells are seeded into the reactor in an appropriate amount. For example, such amount can be about $3$-$6 \times 10^3$ cells/cm², such as about $4$-$5 \times 10^3$ cells/cm², such as $4.5 \times 10^3$ cells/cm². The cells are grown for sufficient time, generally 8 days to 20 days depending on growth conditions, to reach an optimal density for infection with the virus, such as, for example, about $1$-$3 \times 10^5$ cells/cm², such as about $1.5 \times 10^5$ cells/cm². The skilled person knows or can empirically determine optimal densities for growth and infection of particular cells.

In an exemplary process, cells are seeded into the reactor at 4.5E3 cells/cm², and grown to an optimal infection density of 1.5E5 cells/cm², which can take about 8 days to 20 days depending on growth conditions. The cells are infected at a specific MOI (0.2 to 0.002, such as 0.02 to 0.1), and virus production proceeds for about 96 hours. Because the purification is only a single step (ultrafiltration and/or diafiltration), it can be conducted in a single day compared to conventional purifications which are typically 5-7 steps conducted over a number of days.

In some embodiments, the bioreactor can be adapted for growth of adherent cells; the iCellis® bioreactor; include elements as disclosed in U.S. Pat. Nos. 8,597,939 and 8,986,979; contain a matrix or surface onto which adherent cells may attach; contain a non-fixed attachment surface such as microcarrier beads, fibers, or woven mesh in suspension; and/or contain a fixed attachment surface as in a packed bed bioreactor.

In some embodiments adherent host cells are cultured in the bioreactor under controlled conditions; in the presence of cell culture medium and medium additives that support the nutritional requirements of the cells; at a temperature suitable for optimum growth of the cells (e.g., 37±3° C. for mammalian cells); at a pH suitable for optimal growth of the cells (e.g., pH 7.3±3 for mammalian cells); with agitation or circulation of the medium or culture suitable for optimal growth of the cells; in a fixed bed reactor at a linear flow velocity of medium at about 0.5 to 5 cm/second; at a dissolved oxygen level suitable for optimal growth of the cells (e.g., 50±25% for mammalian cells); and/or to high cell density relative to the medium volume of the bioreactor (e.g., ≥2×10E6 cells/mL, or 1×10E7 cells/mL).

E. Virus and Inoculation

The viruses contemplated herein, include, but are not limited to, therapeutic viruses, such as oncolytic viruses, viruses for vaccines, and viruses for any purpose, including for recombinant production of an encoded product. The viruses generally are enveloped viruses that can be released to the cell culture medium.

The virus is introduced into the cells, which then are cultured so that the virus replicates. The cells are infected at a specific multiplicity of infection (MOI), which depends on the virus. In exemplary embodiments, the virus is a vaccinia virus, and the MOI is about 0.002. Virus production proceeds for a time to result in maximum amount of virus, such as, for vaccinia, such as the virus designated GL-ONC1 (GLV1h-68), about 72-120, such as 90-120, such as 96, hours.

The host cells can be infected with the virus before being introduced to the bioreactor, or the adherent host cells can be infected with the virus while growing in the bioreactor. Bioreactor medium and/or other culture conditions can be adjusted before or after introduction of infected or uninfected host cells to optimize infection efficiency and/or replication of the virus.

Viruses include, but are not limited to, poxviruses, herpesviruses, adenoviruses, adeno-associated viruses, lentiviruses, retroviruses, rhabdoviruses, papillomaviruses, vesicular stomatitis virus, measles virus, Newcastle disease virus, picornavirus, Sindbis virus, papillomavirus, parvovirus, reovirus, coxsackievirus, influenza virus, mumps virus, poliovirus, and semliki forest virus.

The virus can be native; wild-type; recombinant; or genetically modified. The virus can selected from among a Newcastle Disease virus, parvovirus, vaccinia virus, myxoma virus, measles virus, reovirus, vesicular stomatitis virus (VSV), oncolytic adenoviruses, adeno-associated virus, poliovirus, herpes viruses, Sindbis virus and Seneca Valley virus, or a derivative thereof that is modified to contain a nucleic acid encoding a heterologous gene product. The virus can be an oncolytic virus. The oncolytic virus can be a vaccinia virus, wherein the vaccinia virus is selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63, and NYVAC strains. The vaccinia virus can be derived from a Lister strain virus: an LIVP virus or a clonal strain of an LIVP virus.

The virus can be a vaccinia virus, such as a recombinant vaccinia virus. Exemplary of therapeutic vaccinia viruses are the modified LIVP strain viruses, such as those described in U.S. Pat. Nos. 7,588,767, 8,857,927, 9,005,602, 8,323,959 and 7,754,221, particularly, the virus designated GLV-1h68 (GL-ONC1), and the clonal strains described in U.S. Publication No. US-2012-0308484-A1, and modified Wyeth strain vaccinia virus, such as the virus designated JX-594 (also referred to as Pexa-Vec, Sillajen Biotherapeutics), which is a replication-competent Wyeth strain vaccinia virus that is modified so that the thymidine kinase gene is inactivated, and the virus encodes and expresses the human GM-CSF and LacZ genes.

The virus can be a modified form containing a nucleic acid encoding a heterologous gene product, wherein the heterologous gene product is a therapeutic or reporter gene product. The heterologous gene product is selected from among an anticancer agent, an antimetastatic agent, an antiangiogenic agent, an immunomodulatory molecule, an antigen, a cell matrix degradative gene, genes for tissue regeneration and reprogramming human somatic cells to pluripotency, enzymes that modify a substrate to produce a detectable product or signal or are detectable by antibodies, proteins that can bind a contrasting agent, genes for optical imaging or detection, genes for PET imaging and genes for MRI imaging. The heterologous gene product can be a therapeutic agent selected from among a hormone, a growth factor, cytokine, a chemokine, a costimulatory molecule, ribozymes, a transporter protein, a single chain antibody, an antisense RNA, a prodrug converting enzyme, an siRNA, a microRNA, a toxin, an antitumor oligopeptide, a mitosis inhibitor protein, an antimitotic oligopeptide, an anti-cancer polypeptide antibiotic, an angiogenesis inhibitor, a tumor suppressor, a cytotoxic protein, a cytostatic protein and a tissue factor. The viruses can encode and, if desired, express heterologous gene products. The products include therapeutic products that can be delivered by the virus. Exemplary of such products is an anticancer agent, an antimetastatic agent, an antiangiogenic agent, an immunomodulatory molecule, and an antigen. Other exemplary products, include, but are not limited to, a therapeutic agent selected from among a hormone, a growth factor, cytokine, a chemokine, a costimulatory molecule, ribozymes, a transporter protein, a single chain antibody, an antisense RNA, a prodrug converting enzyme, an siRNA, a microRNA, a toxin, an antitumor oligopeptide, a mitosis inhibitor protein, an antimitotic oligopeptide, an anti-cancer polypeptide antibiotic, an angiogenesis inhibitor, a tumor suppressor, a cytotoxic protein, a cytostatic protein and a tissue factor. Viruses also can deliver nucleic acids encoding genes, such a cell matrix degradative gene, genes for tissue regeneration and reprogramming human somatic cells to pluripotency. The viruses can encode detectable reporter products, such as, but are not limited to, enzymes that modify a substrate to produce a detectable product or signal or are detectable by antibodies, proteins that can bind a contrasting agent, genes for optical imaging or detection, genes for PET imaging and genes for MRI imaging.

F. Cell Lysis and Release of Virus into the Process Medium

In the production stage of the process, the cells in the bioreactor are lysed, and treated to release the virus. In accord with the methods herein, the virus can be released from host cells without substantial mechanical homogenization.

This can be effected by any suitable method for lysing cells. The lysis method should be such that the cells remain adhered to or are entrapped in the matrix. For example, the cells are lysed by freezing and thawing. Optionally, release and recovery of the virus can be enhanced by hypotonic shock. This can be effected, for example, by addition of aqueous solutions with total ionic strength less than approximately 0.05 M, such as 0.01 M or less, or such as 0.001 M to the freeze/thawed bioreactor.

By virtue of the selected matrix, the cells and lysed cell debris remains attached/entrapped in the matrix and is not released, or is substantially not released, into the cell culture medium with the virus. Release of the virus from the entrapped/adhered cells is effected by suitable methods to effect lysis, such as freeze/thaw of the bioreactor and/or exposure to hypotonic medium, and, then, enzymatic digestion with enzymes, such as proteases and, optionally, nucleases. Proteases include trypsin or other such proteases normally used to detach cells, but that by virtue of the matrix do not detach the cells. Exemplary of such proteases, are trypsin (porcine pancreatic source), TrypLE (recombinant bacterially-produced enzyme with trypsin-like enzymatic activity), Accutase® solution (Sigma Aldrich; a mixture of proteolytic and collagenolytic enzyme activities), proteinase-K, papain and subtilisin, other such protease with nonspecific cleavage sites to digest proteins, bromelain, ficain, and others.

The virus can be released from host cells by a process involving freeze/thaw. For example, the virus can be released from cells in a fixed bed reactor in a process where the culture medium is removed and the bioreactor is frozen at about ≤10° C. for ≥60 minutes, or at <−60° C. for ≥15 minutes, or at ≤−120° C. for ≥1 minute, or other suitable combination of temperature. The bioreactor can be frozen, for example, by placing it into a freezer, by jacketed refrigeration, by immersion in dry ice, by immersion in liquid nitrogen, by infusion of liquid nitrogen vapor, or other such methods. The bioreactor can be thawed by suitable methods, such as exposure to room temperature air, by addition of liquid medium, such as phosphate buffered saline (PBS), or by other such methods known to those of skill in the art. For example, liquid medium can be added to the bioreactor at a temperature selected to maximize cell lysis while optimizing the stability of the virus (e.g., ≤50° C. or 37±3° C.).

Optionally, if freeze/thaw is employed, release and recovery of the virus can be enhanced by hypotonic shock. Hypotonic shock can be effected, for example, by the addition of aqueous solutions so that the total ionic strength is less than approximately 0.05 M, such as 0.01 M or less, or 0.001 M to the freeze/thawed bioreactor. The virus can be released from host cells by exposure to hypotonic medium. In some embodiments, the hypotonic medium can be water or aqueous buffer with ionic strength ≤50 mM. Hypotonic condition can be accomplished by dilution of the bioreactor medium with hypotonic solution such as water to achieve a final ionic strength ≤50 mM. For example, in a fixed bed bioreactor, the medium can be removed and replaced with hypotonic medium of ionic strength ≤50 mM. In some embodiments, the hypotonic medium can be agitated or circulated.

Optionally, release and recovery of the virus can be enhanced by treatment with an enzyme with DNase and/or RNase activity either during or after the freeze/thaw and/or hypotonic shock or after in a suitable buffer. Exemplary of a nuclease is the endonuclease sold under the trademark Benzonase® endonuclease or other enzyme with DNase and/or RNase activity. Benzonase® nuclease (Sold by Millipore; see, e.g., Franke et al., (1998) FEBS Letters 425: 517-522), which digests native or heat-denatured DNA and RNA, is a genetically engineered endonuclease from *Serratia marcescens*. Known to those of skill in the art as *Serratia* nuclease, it is a protein dimer of 30 kDa subunits with two essential disulfide bonds.

Conditions for releasing the virus from host cells can be selected to maximize cell lysis while optimizing the stability of the virus. For example, the temperature can be ≤50° C.; the pH can be ≥4 and ≤10; and/or the linear flow velocity through a packed bed bioreactor can be ≥2 cm/sec.

The virus can be released from host cells by exposure to medium containing detergent. The detergent can be ionic, cationic or anionic. The concentration of detergent can be, for example, ≤1%.

After treatment with freeze/thaw and optional hypotonic medium and other such treatments, the cells are treated with proteases, as discussed above. The virus can be released from host cells by digestion with one or more enzymes. The cells are exposed to a digestion medium, which has an ionic strength and pH optimal for the selected digestive enzyme (s). Exemplary digestion medium can be buffered at pH ≤8, such as neutral pH between 7 and 8, such as pH 7.4, such as can be PBS. Digestion medium contains a sodium salt; and/or contains a magnesium salt. The digestive enzyme can be a protease, as discussed above, such as trypsin, or recombinant trypsin (TrypLE). The protease treatment can be effective combined with or replaced with a nuclease such as the endonuclease from *Serratia marcescens* sold as Benzonase®. Digestion can employ the nuclease and the protease sequentially or in combination. Digestion temperature can be set to optimize enzymatic digestion and optimize stability of the virus (e.g., 37° C.). The digestion time can be set to optimize enzymatic digestion and optimize stability of the virus (e.g., ≥1 hour). The virus can be harvested by removing the digestion medium, and purifying the virus therefrom.

The released virus can be rinsed with medium selected to optimize virus recovery and/or virus stability. For example, the rinsing medium can be water; can be a buffer of low ionic strength; can be a buffer of high ionic strength; has a pH ≥9; and/or can be 10 mM Tris-Cl, pH 9.0.

G. Diafiltration and Ultrafiltration of the Process Medium to Purify Virus

The purification process, following release of the virus from the cells and enzyme digestion is a single (or dual) step of ultrafiltration or diafiltration or both. No other purification steps are employed or needed. Purification can be conducted in a single day. Conventional prior art purifications typically employ 5-7 steps conducted over a number of days. Not only is there a reduction in time and a cost savings and higher yield by virtue of the purification method provided herein, the fewer steps and shorter time reduces degradation and inactivation of the virus that occurs over time during processing.

The released virus in the culture medium is purified by ultrafiltration or diafiltration, or both. No other purification steps are employed. The released virus can be purified by ultrafiltration. The skilled person can select appropriate filtration membranes and protocols. In some embodiments the filtration medium can be chosen to optimize removal of impurities and optimize stability of the virus; can be water; can be an aqueous buffer; can be high ionic strength; can be low ionic strength; can be physiological ionic strength;

and/or can be suitable for administration to animals or humans. The recovery of processed released virus can be greater than 50%; greater than 70%; greater than 80%; greater than 90%; or greater than 95%.

Ultrafiltration

The virus can be purified using large porosity ultrafiltration membranes typically used to remove contaminating viruses from biopharmaceutical preparations. Such membranes typically have porosities of greater than or equal to 300,000 daltons molecular weight cut off such that protein products pass through the membrane while viruses are retained. Using these "virus clearance" membranes in the opposite mode (tangential flow or cross flow filtration mode rather than a single pass-through mode) viruses can be retained and purified while proteins, nucleic acids and other impurities are removed.

For example, the ultrafiltration membrane can be chosen to minimize virus binding and maximize virus retention. The ultrafiltration membrane can be one that has a porosity with a permeability cut off to prevent virus passage through the pores. For example, the ultrafiltration membrane has a nominal molecular weight cut off of between 300 and 750 kilo-daltons or a nominal porosity between 0.05 and 0.2 μm; the ultrafiltration membrane includes polyethersulfone (PES); the ultrafiltration membrane can be, for example, a flat membrane or a hollow fiber membrane; ultrafiltration can be performed in a tangential flow or cross flow mode; ultrafiltration can be performed under conditions to optimize virus retention and optimize virus stability and/or ultrafiltration can be performed at ≤10° C.

Flat membrane filters and hollow fiber filters can be used for ultrafiltration. Membranes composed of materials that have low binding of virus are suitable for high virus recovery. Examples of such membranes, include, but are not limited to Centramate T-series cassette flat membranes (300 kd mwco, PALL Life Sciences, Inc.) and MidiKros hollow fiber membrane cartridges (500 or 750 kd mwco, Spectrum Laboratories, Inc.), all composed of polyethersulfone (PES).

Diafiltration

Ultrafiltration can be followed by diafiltration with high ionic strength, neutral pH and/or low ionic strength, high pH filtration solutions. As disclosed herein, such methods are capable of recovering greater than 90% of the virus from the lysed cells at high purity.

In some embodiments, the released virus can be purified by diafiltration. In some embodiments, diafiltration can be performed with a membrane chosen to minimize virus binding and maximize virus retention; the diafiltration membrane can be the same one used for ultrafiltration; diafiltration can be performed by addition of filtration medium to the ultrafiltration retentate; and/or diafiltration can be conducted by addition of ≥5 filtration volumes, each equivalent to the retentate volume.

As much as 95% of virus can be recovered. The resulting virus is any virus of interest, particularly vaccinia virus. The virus can be biologically active, can be used to infect cells, can be used to express homologous or heterologous genes or proteins, and/or can be used to elicit an immunological response.

Those skilled in the art can devise many modifications and other embodiments within the scope and spirit of the presently disclosed inventions. Indeed, variations in the materials, methods, drawings, experiments examples and embodiments described may be made by skilled artisans without changing the fundamental aspects of the disclosed inventions. Any of the disclosed embodiments can be used in combination with any other disclosed embodiment.

H. Examples

The following examples are not intended to limit the scope of the disclosure or the claims nor to represent that the experiments below are all or the only experiments performed. Efforts have been made to ensure accuracy with respect to numbers used (e.g., amounts, temperature and other parameters) but some experimental errors and deviations should be taken into account. It should be understood that variations in the methods as described can be made without changing the fundamental aspects that the experiments and examples illustrate.

Example 1

General Methods

CV-1 Cell Cultivation.

All CV-1 cells used in these experiments were derived from CV-1 Working Cell Bank (WuXi Apptec Acc #09-002346, Lot #090170885, $6.0\times10^6$ cells/vial in 1.0 mL, Freeze date 9 Dec. 2009, Passage 45). These cells were further expanded and cryopreserved at passage 55. Aliquots of these cells were used in the iCellis® bioreactor Nano experiments. CV-1 cells were cultivated in DMEM supplemented with 10% FBS in T-flasks and roller bottles in 37° C., 5% $CO_2$ incubators.

Infection with GLV-1h68.

iCellis® bioreactor Nano experiment cultures were infected with GLV-1h68, a recombinant vaccinia virus derived from the LIVP strain. GLV-1h68 P3 2-28-14 was used for infection of Nano Experiments 1-6 and GLV-1h68 P3 8-28-14 for Nano Experiments 7-11. The amount of seed virus used was calculated based on the cell number at time of infection, the titer of the seed virus, and the specified MOI.

iCellis® Bioreactor Nano Bioreactor Procedures.

The iCellis® bioreactor Nano Bioreactor was set-up and operated according to the manufacturer's recommended procedures ("Integrity iCellis® bioreactor Nano Bioreactor with Control System User Guide"-Document reference USG_nano_mycontrol_01, version 01, February 2014.)

Analyses.

Viral Plaque Assay (VPA) was conducted on bioreactor and purification samples infected with GLV-1h68. Samples of reactor medium were removed and frozen at −20° C. Samples of macrocarrier (the matrix) in the bioreactor containing 1 or 2 carriers were removed from the bioreactor and placed in a microcentrifuge tube containing 1 mL of fresh DMEM-10% FBS medium and frozen at −20° C. Prior to testing, medium and carrier samples were thawed at room temperature or 37° C., diluted in DMEM-2% FBS and plated on CV-1 cells for plaque formation. Trypsinization of carriers was conducted by placing one carrier into 0.5 mL of 0.05% Trypsin/0.53 mM EDTA or 1×TrypLE in PBS and incubating at 37° C. for up to 60 minutes with intermittent vortex mixing. Samples were diluted by addition of 1.0 mL of DMEM-10% FBS. Purification samples were stored on ice and tested without prior freezing. VPA was conducted using CV-1 cells according in 24-well multi-well plates. Viral plaques were visualized by crystal violet staining.

ß-Glucuronidase Assay (GUS-A) was conducted on samples of reactor medium and macrocarriers, diluted in DMEM-2% FBS and tested. The fluorogenic substrate Cl-MUGlcU (stock solution: 36.5 mM in DMSO) was used in assay buffer consisting of phosphate buffered saline solution containing 2% FBS. Assays were carried out in 96-well multi-well plates and read in the SpectraMax® M5 plate reader using SoftMaxPro v5.4.4 software.

Protein and DNA content were measured using Quant-iT Protein Assay Kit (Invitrogen®) and Quant-iT dsDNA Assay Kit (high sensitivity, Invitrogen®), respectively. Assays were carried out in 96-well multi-well plates and read in the SpectraMax® M5 plate reader using SoftMaxPro v5.4.4 software.

Example 2

CV-1 Cell Culture Process Development in the iCellis® Bioreactor Nano Bioreactor The seeding density for all experiments was $4.5 \times 10^4$ cells/cm$^2$, matching the seeding density of CV-1 cells in roller bottles. The target cell density for infection was 1.0 to $2.0 \times 10^5$ cells/cm$^2$.

Figure 2:
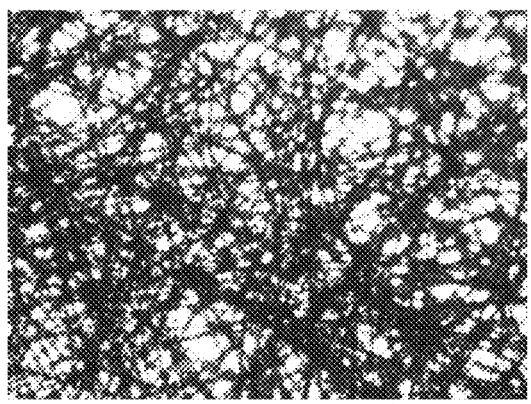
FIG. 2 shows micrographic images of the crystal violet stained carriers from the iCellis® Nano bioreactor Experiment 6, below.
Figure 2:
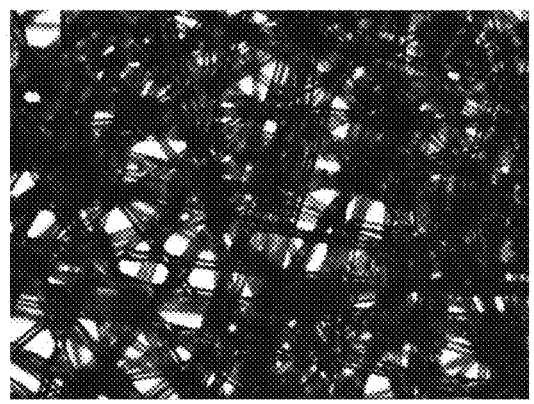
Figure 2:
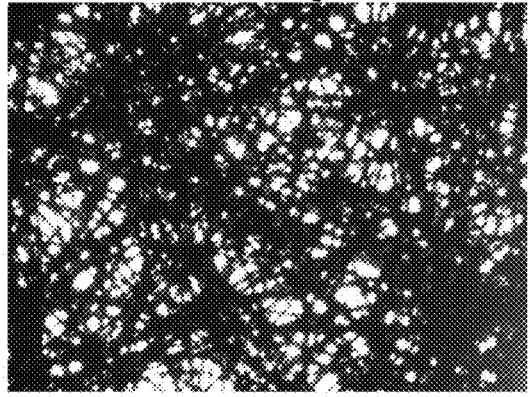
Figure 2:
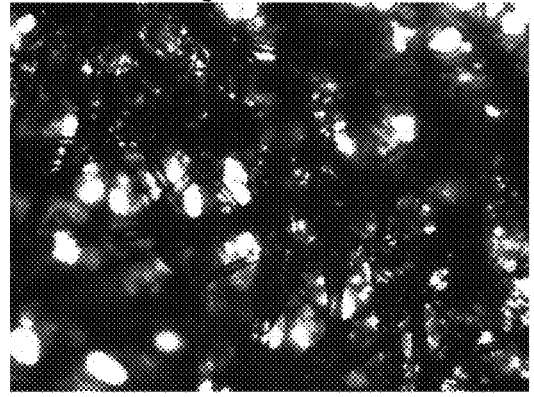
Figure 3:
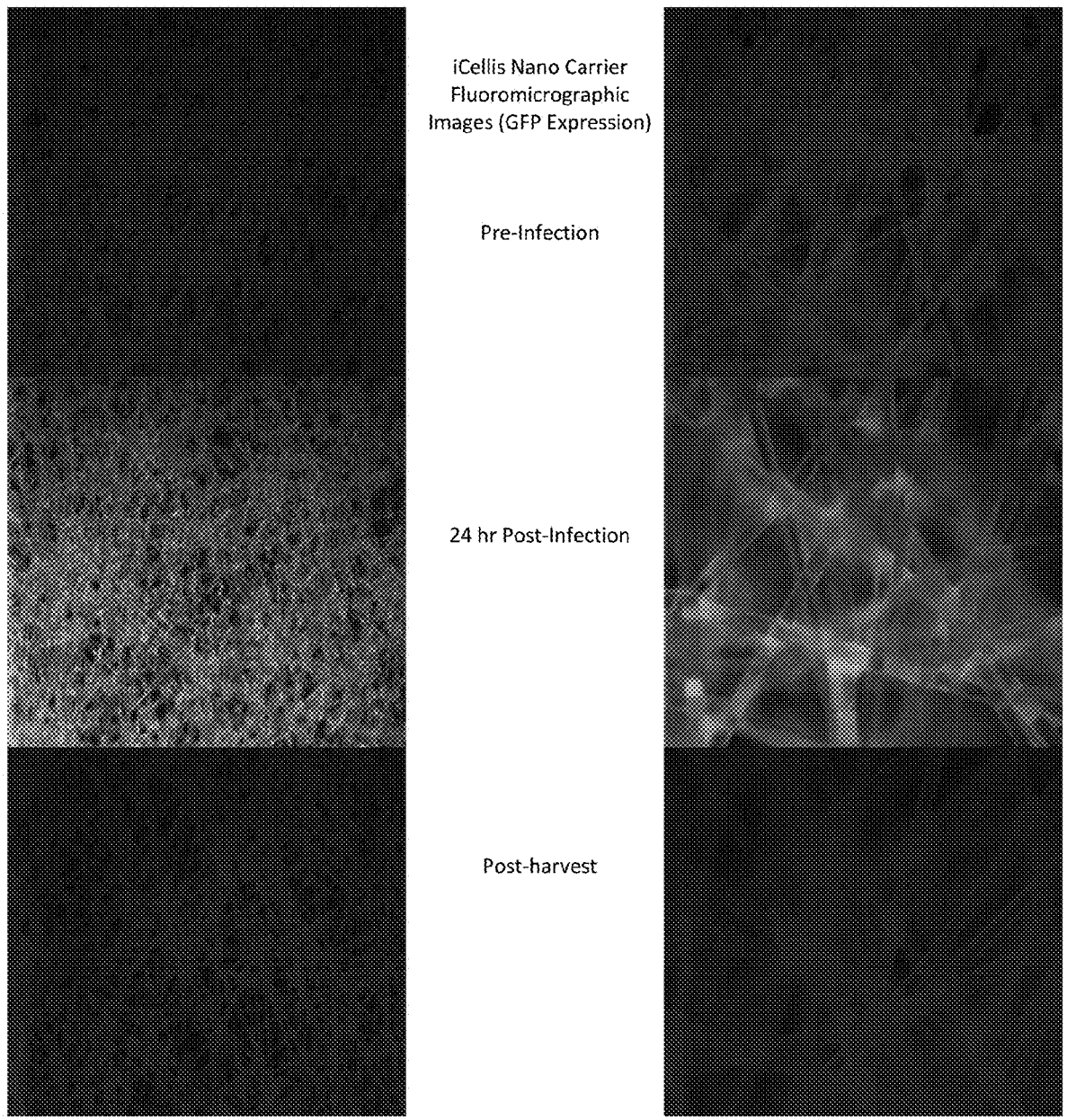
FIG. 3 shows fluoromicrographic images of iCellis® Nano bioreactor carriers before and after infection with the therapeutic LIVP strain vaccinia virus designated GLV-1h68 (also designated GL-ONC1).
Figure 4:
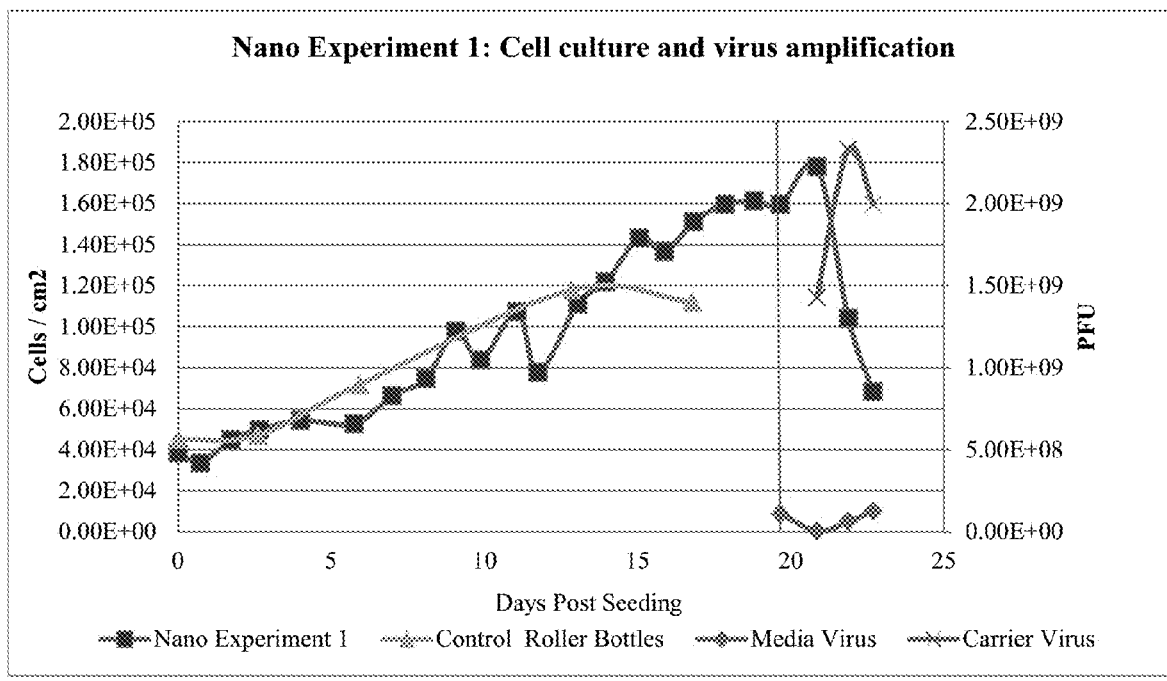
FIG. 4 shows CV-1 cells (widely available well-known cell line, e.g., ATCC® CCL-70 growth profile and virus amplification of iCellis® bioreactor Experiment 1 and roller bottle controls.
Figure 5:
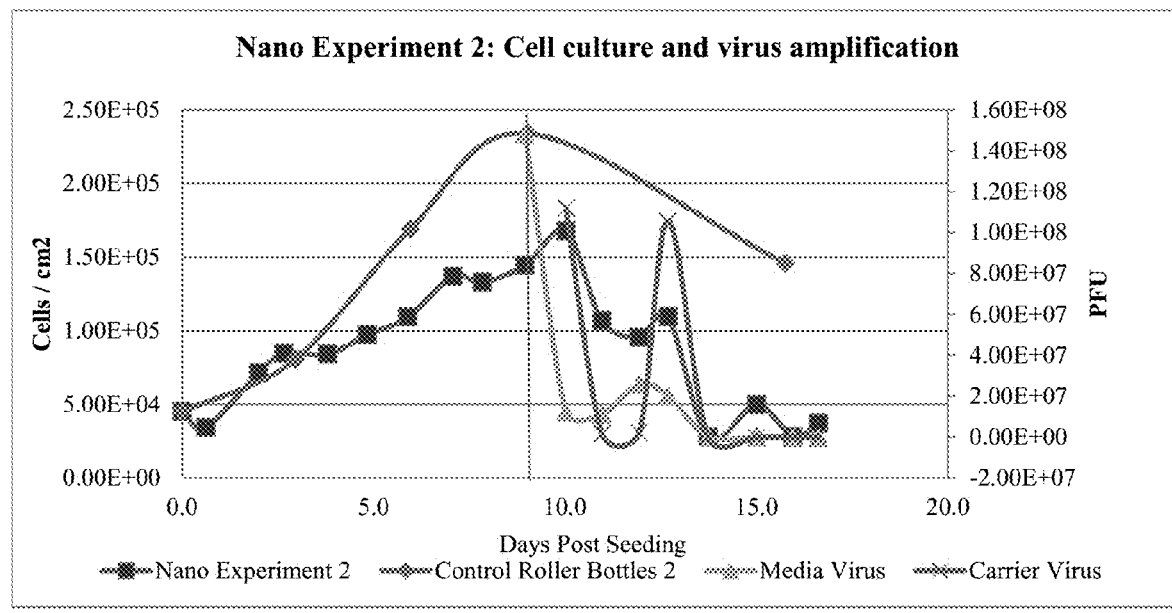
FIG. 5 shows CV-1 growth profile and virus amplification of iCellis® bioreactor Experiment 2 and roller bottle controls.

Culture progress was assessed by aseptically opening the bioreactor and removing carriers at various times during the culture process. The cells attached to the carriers were lysed and cell nuclei were counted using a hemocytometer. Cells were also visualized microscopically on the carriers by crystal violet staining. Micrographic images of the stained carriers of Experiment 6 are shown in FIG. 2. Prior to cell seeding, the carrier fibers appeared uniform in diameter and lacked appreciable staining. Post-seeding the carriers appeared to have accumulated stained material both attached to individual fibers and in the interstitial spaces between fiber bundles. The stained material constituted the cells that had attached to the fibers and to each other as they propagated. After infection with GLV-1h68, carriers were imaged microfluoroscopically to assess the amount and distribution of GFP expression. FIG. 3 shows carriers at pre-infection, 24 hours post-infection, and post-harvest. Clearly evident was the intense green GFP fluorescence associated uniformly with the fibers 24 hours post-infection. At higher magnification, individual fluorescing centers were observed on the fibers corresponding to the location of the cells. The fluorescence was considerably reduced.

During and after infection, viral titers were assessed to determine the amount of virus amplification and the distribution of the virus between the cells and the culture medium. Carriers were sampled from the reactor and underwent freeze-thaw in fresh culture medium for assay by VPA. The culture medium from the reactor was sampled at the same time and assayed directly by VPA. Virus amount was either expressed as PFU/cm$^2$ of surface area, PFU/cell (cell number determined at time of infection), or as total PFU in the reactor (either carrier-associated or in the medium).

Nano Experiment 1

Figure 6:
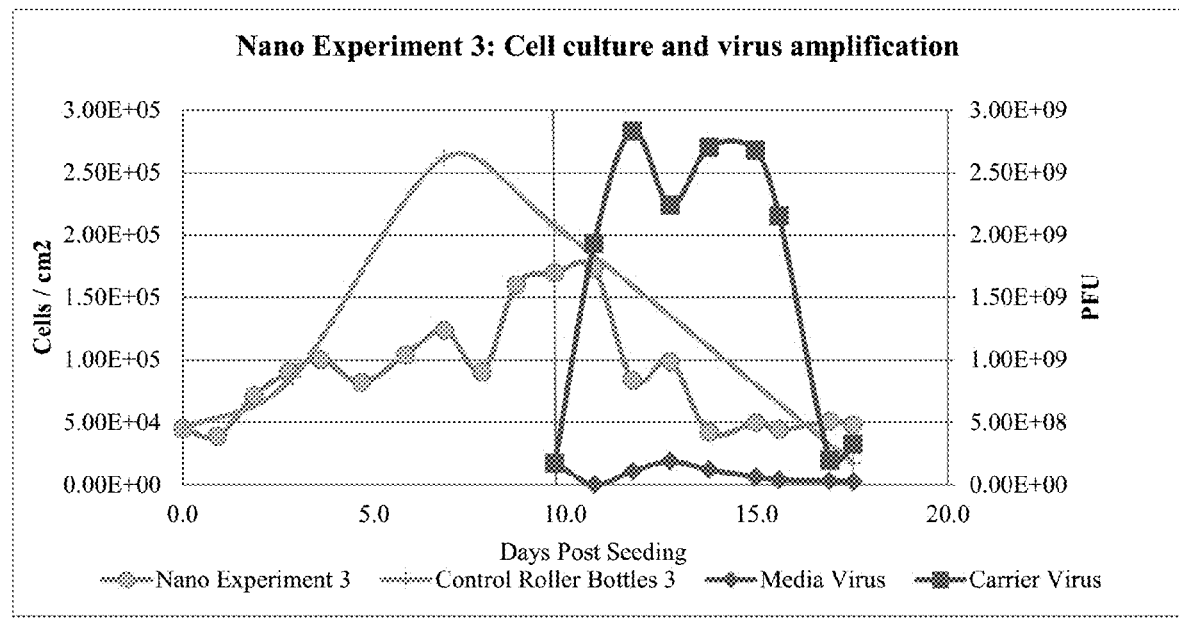
FIG. 6 shows CV-1 growth profile and virus amplification of iCellis® bioreactor Experiment 3 and roller bottle controls.
Figure 7:
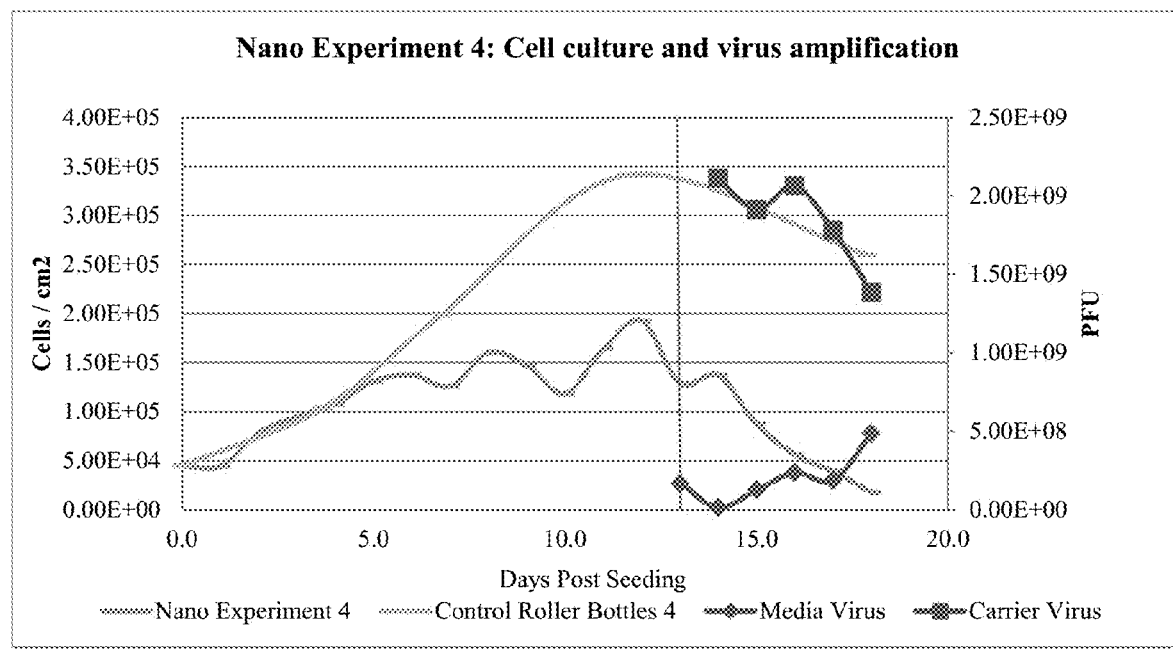
FIG. 7 shows CV-1 growth profile and virus amplification of iCellis® bioreactor Experiment 4 and roller bottle controls.
Figure 8:
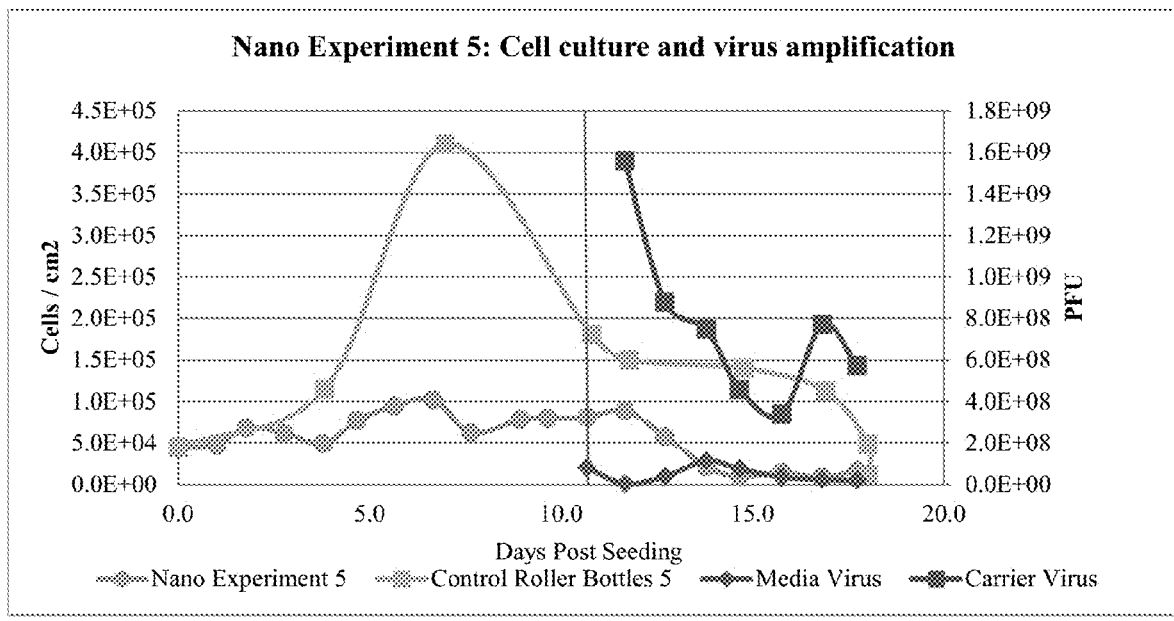
FIG. 8 shows CV-1 growth profile and virus amplification of iCellis® bioreactor Experiment 5 and roller bottle controls.
Figure 9:
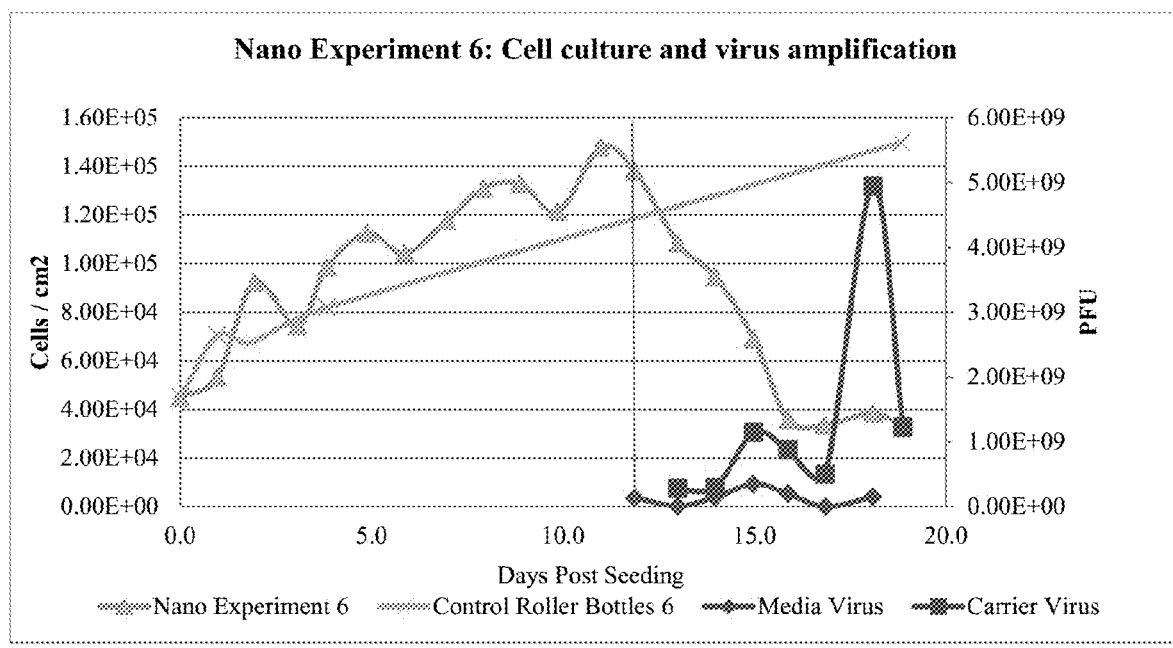
FIG. 9 shows CV-1 growth profile and virus amplification of iCellis® bioreactor Experiment 6 and roller bottle controls.
Figure 10:
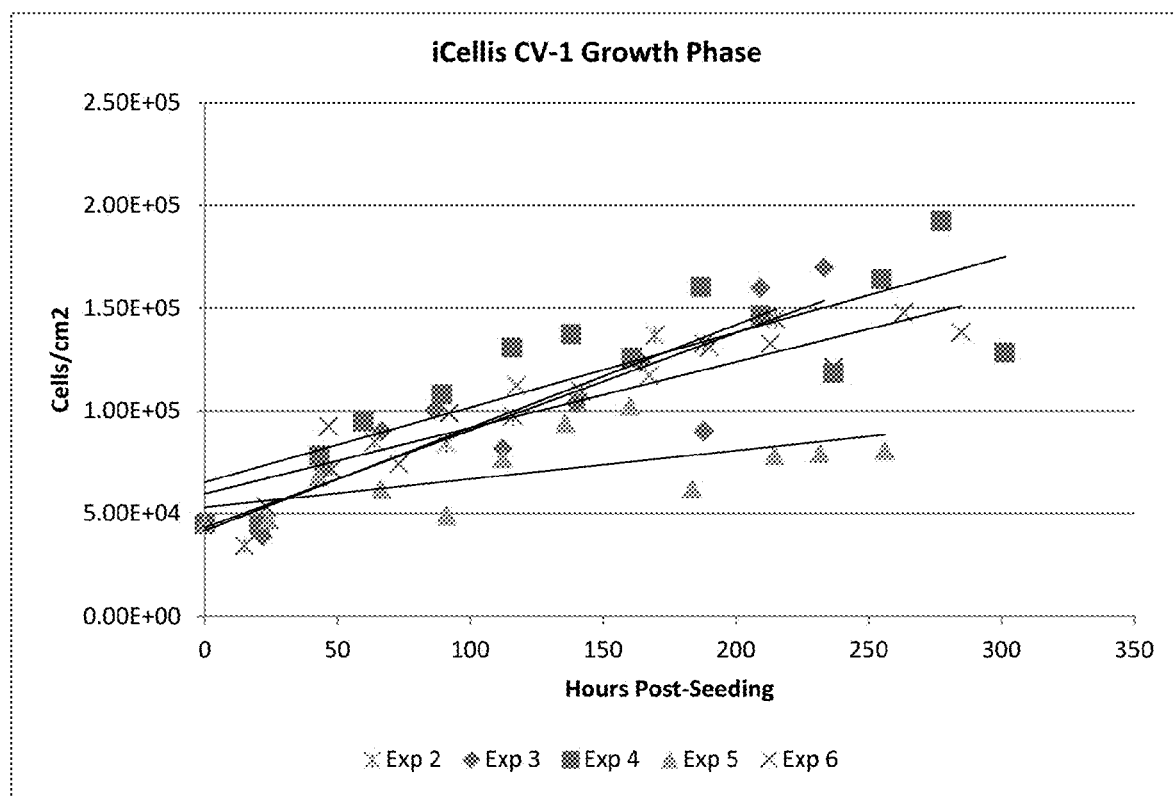
FIG. 10 shows Individual growth curves of iCellis® bioreactor Nano Experiments 2 to 6.
Figure 11:
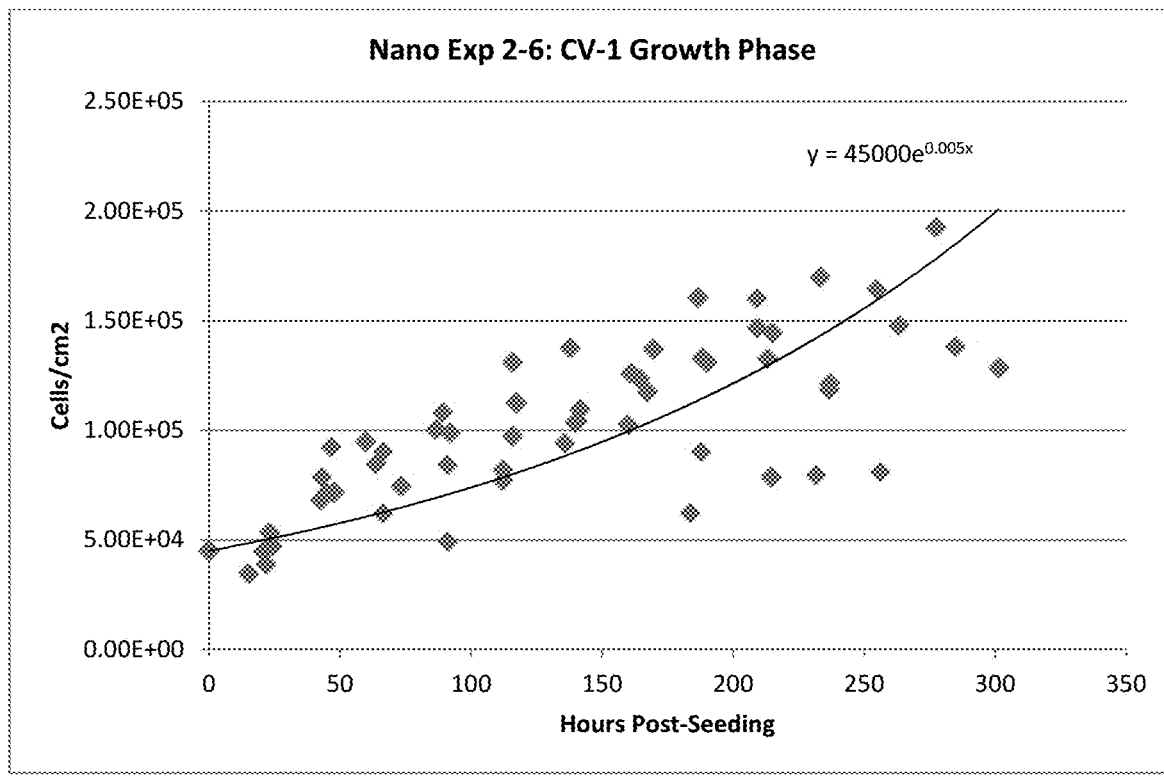
FIG. 11 shows compiled growth data of CV-1 cells in iCellis® bioreactor Experiments 2 to 6 throughout the growth phase.

The reactor was seeded with CV-1 cells of passage 71 at $4.5 \times 10^4$ cells/cm$^2$ and at 24 hours, $3.4 \times 10^4$ cells/cm$^2$ were attached to the bioreactor (76%). The agitation rate of the culture was set to create a linear flow velocity of 1.6 cm/sec during cell seeding and raised to 2.5 cm/sec through Day 10. The flow velocity was reduced to 1.6 cm/sec on Day 10, 1.0 cm/sec on Day 14, and 0.5 cm/sec on Day 16. The volume culture medium was increased from 600 mL to 762 mL after seeding and to 2286 mL on Day 3. The medium was exchanged on Days 3, 6, 10, 14, and 16. On Day 21, the culture was infected with GLV-1h68 at an MOI of 0.07 ($1.12 \times 10^8$ pfu) in 600 mL of DMEM-2% FBS medium. The flow velocity was maintained at 0.5 cm/sec. The culture was harvested 72 hours post-infection. Concurrently, CV-1 cells were seeded into roller bottles and cell counts were performed periodically. Roller bottles were cultured under standard laboratory conditions without changes of culture medium. FIG. 6 shows the cell density profile of the cultures.

The results showed that CV-1 cells seeded into the iCellis@ bioreactor grew throughout the growth period fairly comparably to roller bottle controls. The CV-1 culture in the reactor reached the target $1.6 \times 10^5$ cells/cm$^2$ (approximately 2 population cell doublings), indicating that the bioreactor could support the growth of cells to this density. Neither the changes in agitation rate nor the culture media changes significantly affected the overall growth rate of the cells. During the growth phase, it was observed that the culture medium became cloudy, which is indicative of the possible detachment of cells from the reactor. Lower agitation reduced this.

Infection of the culture with GLV-1h68 on Day 21 caused an immediate increase in the virus titer evident on Day 1 post-infection and reaching a maximum at Day 2. Throughout the 72 hour amplification period, the virus was associated with the carriers (i.e. the cells) and very little was detected free in the medium. There was a decrease in cell number on the carriers over the post-infection period, although this decrease did not correspond with increased virus titer in the medium. On Day 1 post-infection, the culture had acidified to pH 6.2, the medium became cloudy and cell density dropped. To counteract this, an alkali pump was used to deliver a sodium hydroxide solution to the bioreactor. This was used in all subsequent bioreactor experiments.

Nano Experiment 2

Nano Experiment 2 was performed by reducing the flow velocity immediately after cell seeding. The reactor was seeded with CV-1 cells of passage 76 at $4.5 \times 10^4$ cells/cm$^2$ in 600 mL of medium at a linear flow velocity of 1.6 cm/sec. After 1 hour the volume of culture medium was increased to 1342 mL, and the linear velocity was increased to 2.5 cm/sec. After 24 hours the attached cell density was $3.5 \times 10^4$ cells/cm$^2$ (78%). On Day 1, the volume the culture medium was increased to 2286 mL, and the flow velocity was reduced and maintained at 0.5 cm/sec. The culture medium was changed on Day 5.

On Day 10, $1.7 \times 10^5$ cells/cm$^2$ was achieved (more than 2 population cell doublings). The culture was infected with GLV-1h68 at an MOI of 0.1 ($1.48 \times 10^8$ pfu) and the flow velocity was reduced to zero through Day 3 post-infection. Virus levels decreased rapidly in the bioreactor, both on the carriers and in the medium, below the level of the initial infection. Linear velocity was restored on Days 4-8 post-infection but only to very low levels (up to 0.3 cm/sec) in order to circulate nutrients to the cells, but virus levels in the bioreactor remained very low. Efficient virus infection and spreading in the bioreactor was achieved with agitation via circulation of the medium, therefore subsequent experiments were conducted at linear velocities between 0.5-2.5 cm/sec.

Nano Experiment 3

Nano Experiment 3 was a repeat of Experiment 2 except that the linear flow velocity after Day 1 was further reduced to 0.44 cm/sec. The reactor was seeded with CV-1 cells of passage 78 at $4.5 \times 10^4$ cells/cm$^2$ and after 24 hours, $3.9 \times 10^4$ cells/cm$^2$ were attached (87% seeding efficiency).

On Day 10, the cell density had achieved $1.7 \times 10^5$ cells/cm$^2$. On Day 11, the culture was infected with GLV-1h68 at an MOI of 0.1 (1.74×10$^8$ pfu). The flow velocity was increased and maintained at 0.5 cm/sec. The virus increased immediately on the carriers, whereas the virus in the culture medium remained low. Virus amplification was intentionally extended to Day 8 post-infection to examine the full amplification profile. The virus increased through Day 2 post-infection, then remained relatively stable through Day 6, before decreasing significantly at Days 7 and 8. The decrease did not correspond with an increase of virus in the culture medium.

Nano Experiment 4

In Nano Experiment 4 the reactor was seeded with CV-1 cells of passage 81 at 4.5×10$^4$ cells/cm$^2$ and at 24 hours, the cell density was 4.5×10$^4$ cells/cm$^2$ (100% seeding efficiency). After 24 hours, the flow velocity was set at 0.44 cm/sec and the media volume was increased to 2286 mL. There was a single media change on Day 7. On Day 10, the flow velocity was increased and maintained at 1.5 cm/sec.

In this experiment, the cell density increased in the bioreactor steadily until Day 8-10. On Day 11, the linear velocity was increased to 1.5 cm/sec and cell growth resumed, reaching a maximum cell density of 1.9×10$^5$ cells/cm$^2$ on Day 12 (more than 2 population cell doublings).

Infection of the bioreactor on Day 14 (MOI=0.13, 1.72×10$^8$ pfu) produced a maximum virus amplification on Day 1 post-infection. The virus was associated almost exclusively with the carriers. The virus declined on the carriers on Days 4 and 5 post-infection with a corresponding rise in the virus in the culture medium.

Nano Experiment 5

In Nano Experiment 5 CV-1 cells at passage 58 were used directly from cryopreservation. The cells were propagated from the same working cell bank as the CV-1 cells used in the previous experiments.

Nano Experiment 5 was seeded at 4.5×10$^4$ cells/cm$^2$ and at 24 hours, 4.7×10$^4$ cells/cm$^2$ were attached (104% seeding efficiency). The volume of the culture medium was increased to 2286 mL, and the linear flow velocity was set at 0.44 cm/sec. A single change of culture medium occurred on Day 4, and on Day 9 the flow velocity was increased to 0.9 cm/sec.

In this experiment, cell density reached a maximum 1.0×10$^5$ cells/cm$^2$ (approximately 1.5 population cell doublings) on Day 7 and declined thereafter. The increase in flow velocity on Day 9 did not appreciably increase the growth rate. The culture was infected with GLV-1h68 on Day 12 at an MOI of 0.1 (8.26×10$^7$ pfu) and the flow velocity was increased to 2.5 cm/sec. Virus accumulated on Day 1 post-infection, but then declined thereafter. The virus was associated almost exclusively with the carriers, and no appreciable increase of virus in the culture medium occurred.

Nano Experiment 6

Nano Experiment 6 was conducted with CV-1 cells of passage 62, continued passage of the cells used in Experiment 5. The procedure repeated that of Experiment 5, except that no change in the flow velocity occurred during the growth phase after its reduction to 0.44 cm/sec at 24 hours post-seeding and the single change of culture medium did not occur until Day 6. The reactor was seeded with 4.5×10$^4$ cells/cm$^2$ and at 24 hours, 5.3×10$^4$ cells/cm$^2$ were attached to the reactor (118% seeding efficiency).

In this experiment, 1.5×10$^5$ cells/cm$^2$ was achieved on Day 11 (approximately 2 population cell doublings). The culture was infected with GLV-1h68 on Day 12 (M01=0.1, 1.40×10$^8$ pfu), little virus amplification was detected until Day 3 post-infection, and an additional peak occurred on Day 6 post-infection. Again, very little virus was detected in the culture medium.

Analysis of CV-1 Cell Growth Phase in Nano Experiments 1-6

Figure 12:
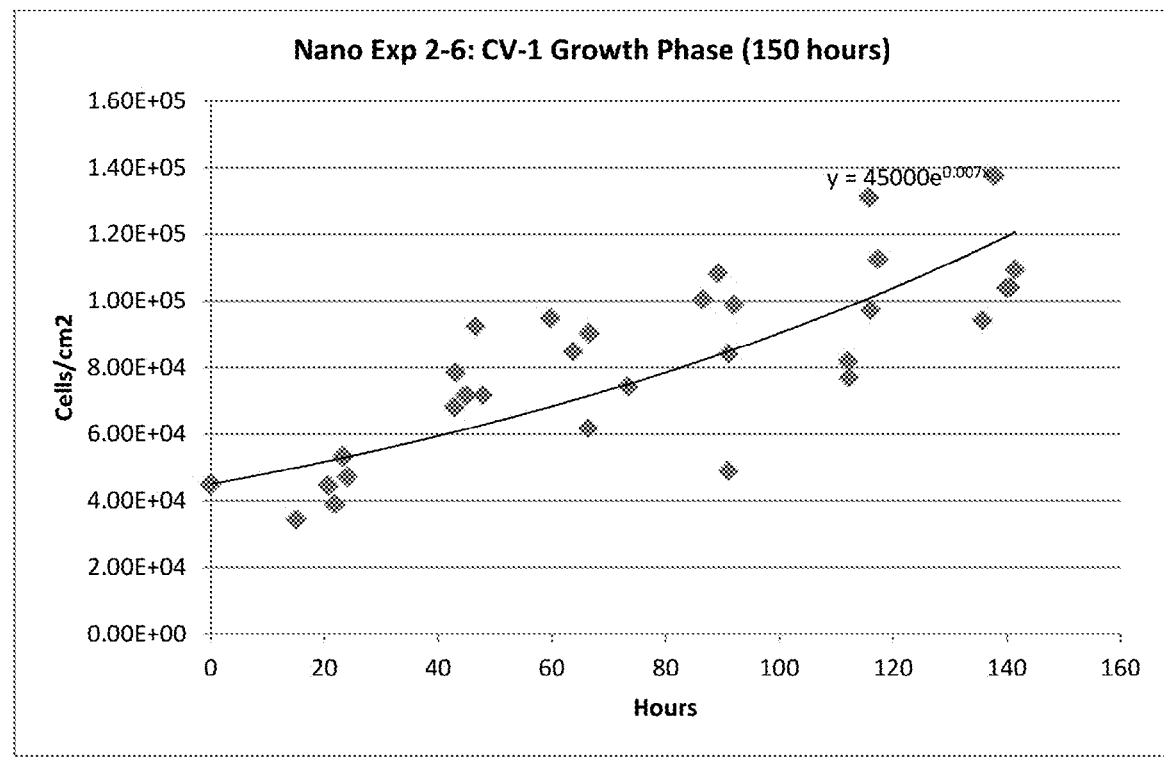
FIG. 12 shows compiled growth data of CV-1 cells in iCellis® bioreactor Experiments 2 to 6 through 150 hours of the growth phase.

CV-1 cell growth was examined for Nano Experiments 2-6. The individual growth curves are displayed in FIG. 12.

Figure 13:
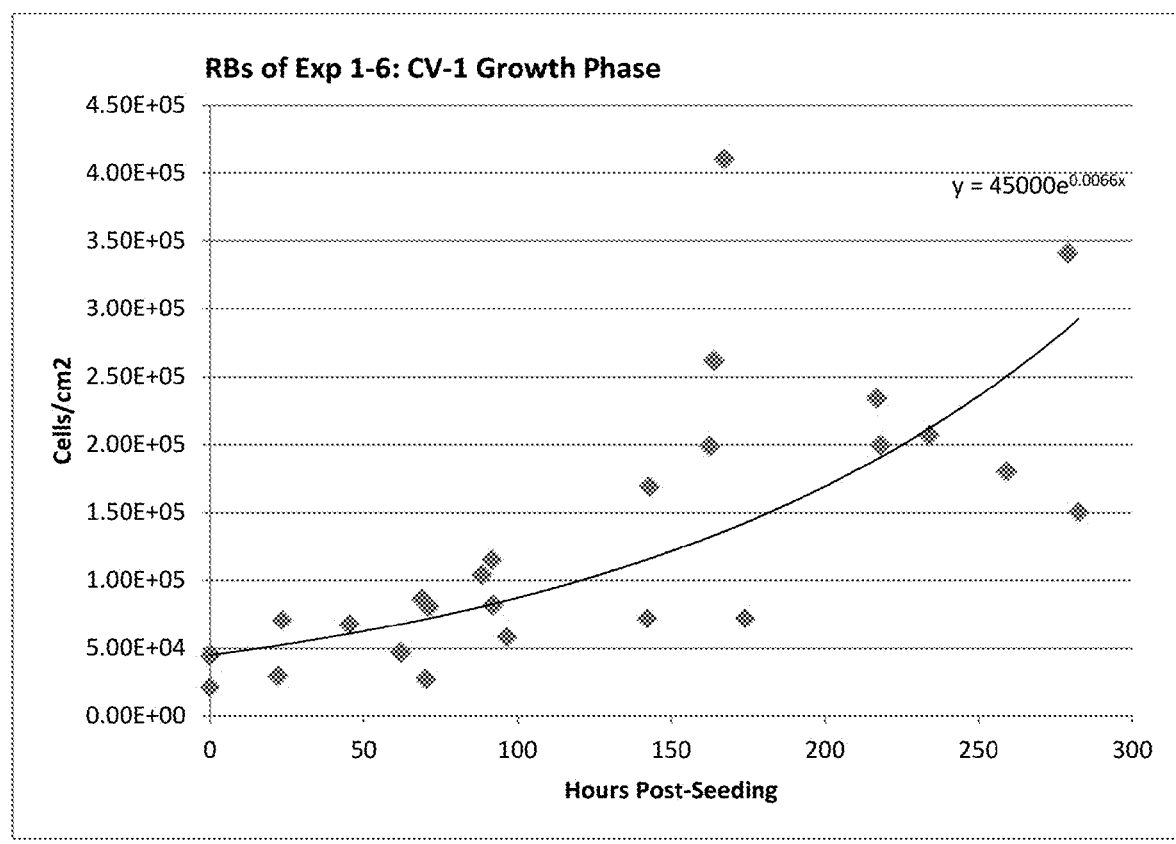
FIG. 13 shows compiled cell density data of CV-1 cells in roller bottle controls of Experiments 1 to 6 through 300 hours of the growth phase.
Figure 14:
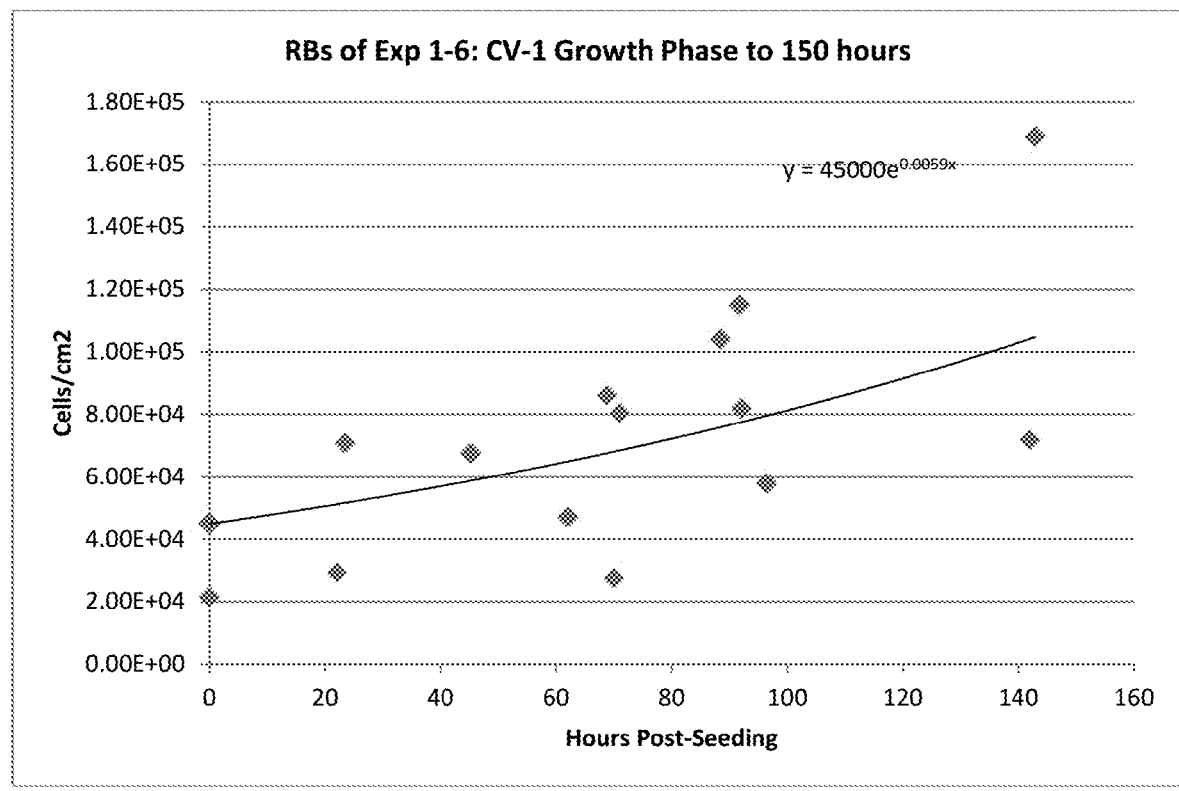
FIG. 14 shows compiled cell density data of CV-1 cells in roller bottle controls of Experiments 1 to 6 through 150 hours of the growth phase.
Figure 15:
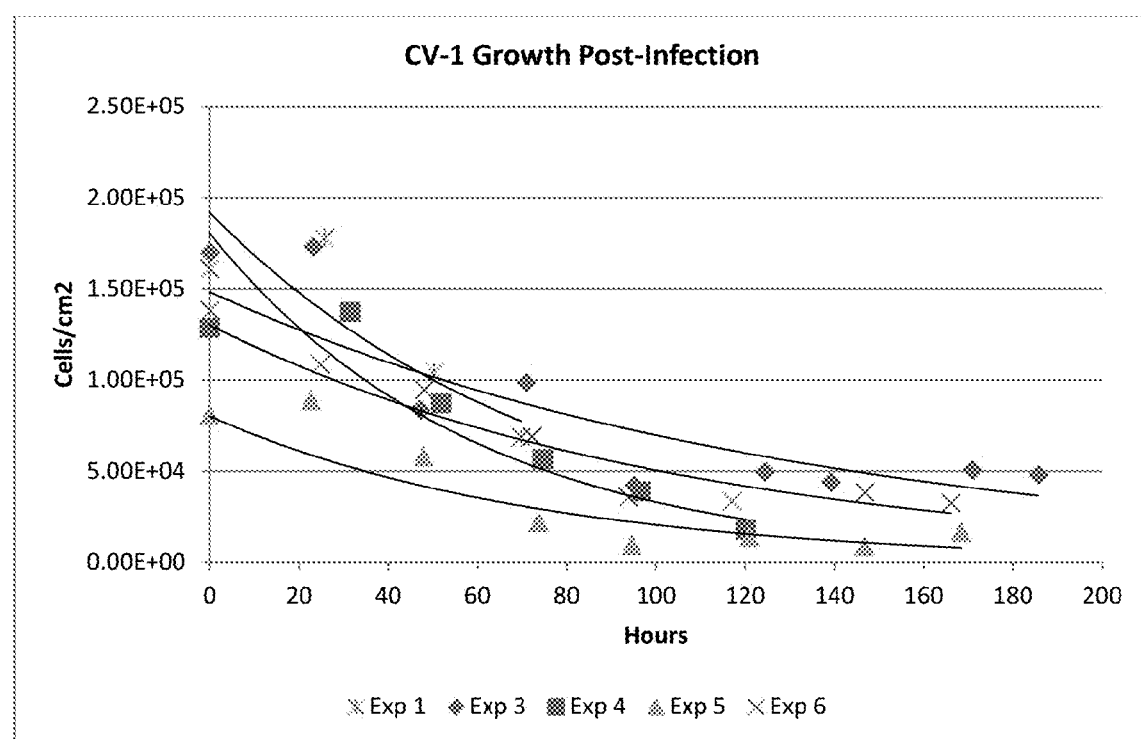
FIG. 15 shows individual growth curves of iCellis® bioreactor Nano Experiments 1 and 3-6 after infection with GLV-1h68.
Figure 16:
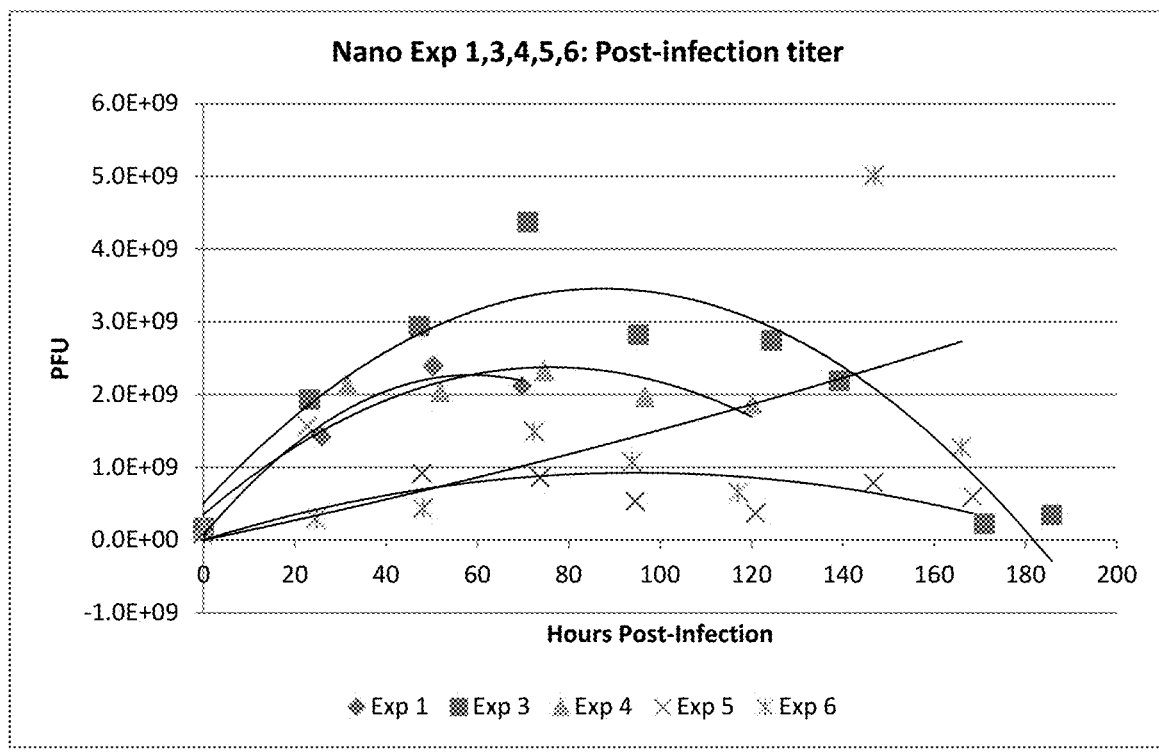
FIG. 16 shows virus amplification data from Nano Experiments 1 and 3-6.
Figure 17:
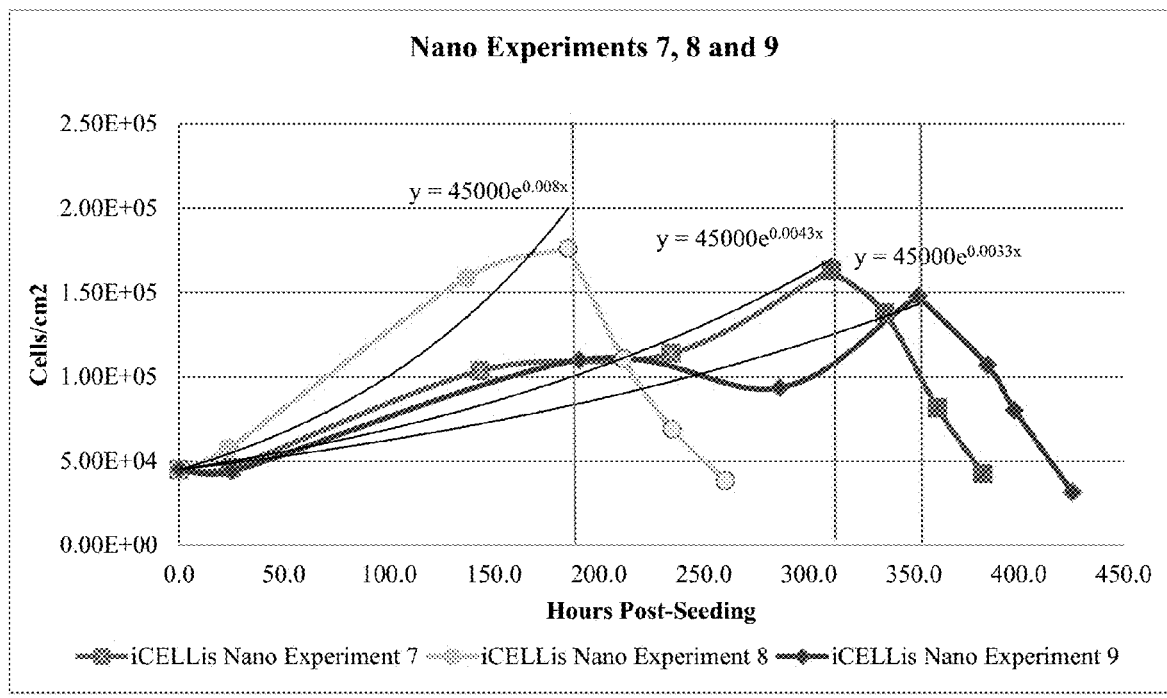
FIG. 17 shows CV-1 growth profile of iCellis® bioreactor Experiments 7, 8 and 9.
Figure 18:
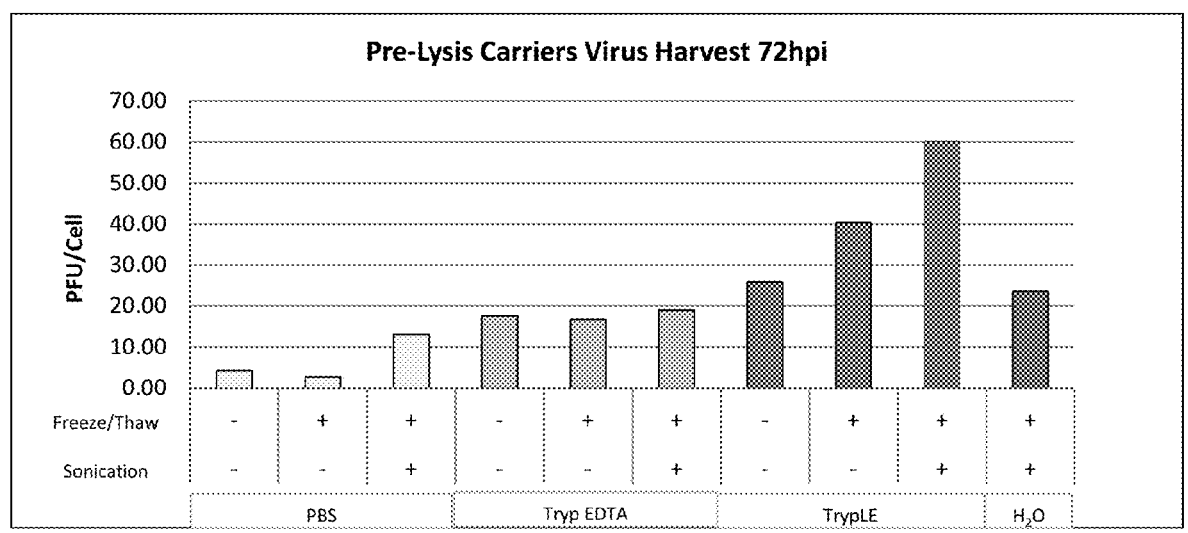
FIG. 18 shows an evaluation of virus extraction conditions from bioreactor carriers (Trial 4).
Figure 19:
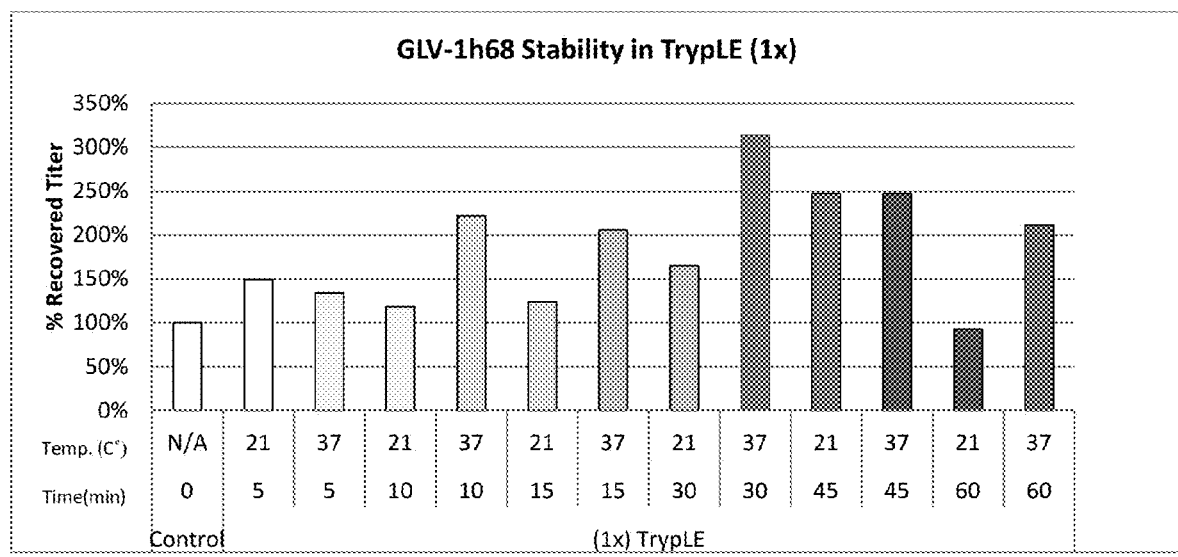
FIG. 19 shows an evaluation of virus stability in TrypLE (Trial 8).
Figure 20:
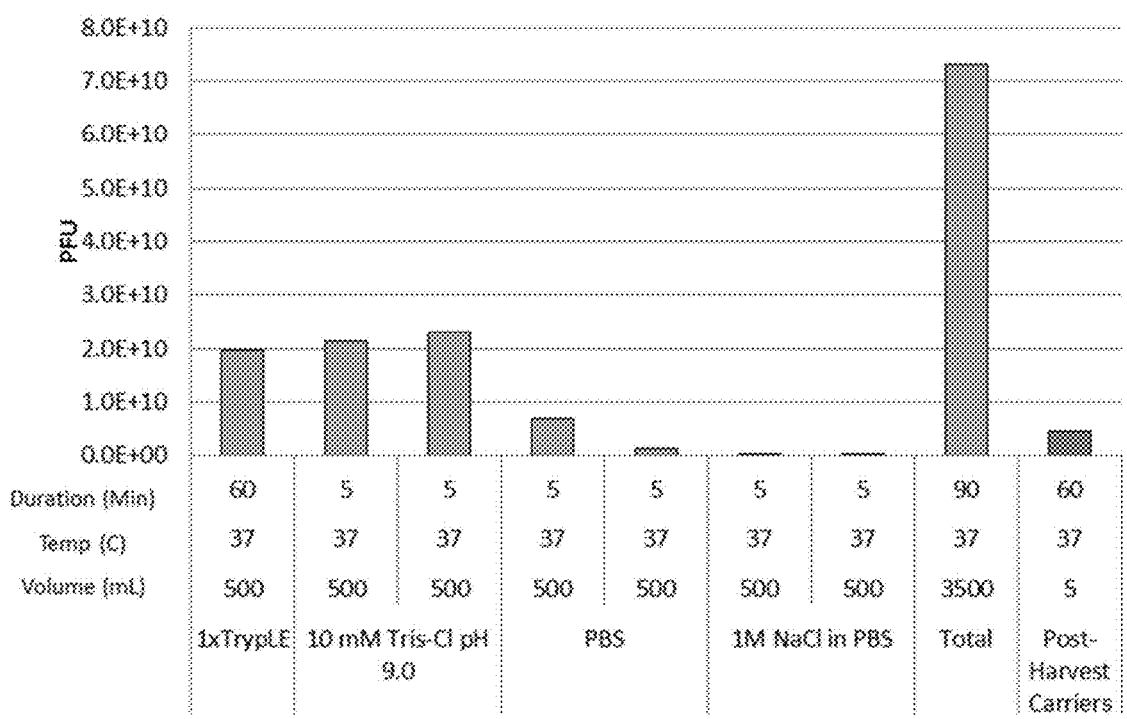
FIG. 20 shows the recovery of virus during the harvest step from the bioreactor. The bioreactor is treated sequentially by circulation of various solutions and processing medium. Recovery of the virus is quantified by testing the collected circulating solution by viral plaque assay. The results show that the majority of the virus is released from the bioreactor after treatment with 1×TrypLE and washes with 10 mM Tris-Cl. Washes with PBS and 1M NaCl do not result in substantial additional virus recovery. Extraction of the bioreactor macrocarriers (matrix) after harvest showed no substantial virus remaining demonstrating the efficiency of the harvest procedure.

The growth data for the 5 experiments were combined, and an overall growth curve was generated. FIG. 13 shows the data fitted to an exponential equation with a time dependency coefficient of 0.005. The population doubling time (PDT), calculated from the growth curve equation for CV-1 cells grown in the bioreactor, was 140 hours.

When the growth data from Experiments 2-6 was truncated at 150 hours post-seeding, the PDT was 99 hours.

Analysis of GLV-1h68 Infection Phase in Nano Experiments 1-6

Within 24 to 48 hours after infection, cell density in the bioreactor declined and continued to decline throughout the infection period. Except for Experiment 1, in which sudden acidification of the culture occurred at 24 hours post-infection, there was no evidence of extensive cell lysis in any of the bioreactor experiments in which pH was adequately controlled. Except for Experiment 6, the decline was not evident at 24 hours post-infection.

Virus production in the iCellis® bioreactor was assessed by sampling carriers and the medium from the reactor every 24 hours after infection. The viral titer of the medium was assayed directly by viral plaque assay (VPA), whereas the carriers were subjected to freeze/thaw in fresh medium and then titered. The results revealed that the virus accumulated in the bioreactor up to 72 hours post-infection and then declined. Based on this analysis, the targeted time for virus harvest from the bioreactor was 72 hours post-infection.

Production of GLV-1h68 in the iCellis® Bioreactor

Three consecutive bioreactor runs were conducted (Nano Experiments 7, 8 and 9). Experiments 7 and 8 were derived from CV-1 cells continuously expanded from the same working cell bank (WCB) stock vial, but of subsequent linear passages. Experiment 9 was expanded from a different vial, but of the same WCB stock. Experiments 7, 8 and 9 also varied slightly in linear flow velocity during the growth phase (0.44, 0.56 and 0.67 cm/sec, respectively). Cell growth of Experiments 7, 8 and 9 proceeded to slightly different endpoints prior to infection (1.6×10$^5$, 1.8×10$^5$, 1.5×10$^5$ cells/cm$^2$, respectively). Experiments 7, 8 and 9 varied from the previous Nano Experiments 1-6 in that GLV-1h68 infection was conducted at MOI 0.2 (3.1×10$^8$, 3.7×10$^8$ and 3.1×10$^8$ pfu for Nano Experiment 7, 8 and 9, respectively) and was amplified for 72 hours post-infection. Finally, minimum sampling of the carriers was done to minimize disturbance of the culture and reduce the depletion of carriers from the bioreactor.

The growth characteristics of the CV-1 cells in bioreactor Experiments 7, 8 and 9 are shown in FIG. 28. The reactors were each seeded with 4.5×10$^4$ cells/cm$^2$. The cells for Experiments 7, 8 and 9 were of passage 65, 77 and 59, respectively. After 24 hours, Experiment 7 had 4.6×10$^4$ cells/cm$^2$ (102% seeding efficiency), Experiment 8 had 5.8×10$^4$ cells/cm$^2$ (127% seeding efficiency) and Experiment 9 had 4.4×10$^4$ cells/cm$^2$ (98% seeding efficiency). The growth rate for Experiment 8 was greater than Experiments 7 and 9. Experiment 8 achieved infection density of $1.8\times10^5$ cells/cm$^2$ on Day 8, prior to its scheduled change in culture medium and therefore had the culture medium was not changed The culture medium Experiments 7 and 9 was changed on Days 10 and 12, respectively. Experiments 7 and 9 achieved infection densities of $1.6\times10^5$ cells/cm$^2$ on Day 13 and $1.5\times10^5$ cells/cm$^2$ on Day 15, respectively. The calculated population doubling time (PDT) for Experiment 8 was 87 hours.

Example 3

Method Development for Extraction of Virus from Bioreactor Carriers

The compiled results of the various virus extraction methods illustrated that the methodology greatly impacted the results (FIG. 24). An almost 60 fold difference in the effectiveness of virus harvest was achieved by changing the extraction procedure. The effect of time, temperature and agitation on virus extraction from the carriers was evaluated. When cells were lysed by hypo osmotic shock and freeze/thaw using 1 mM Tris pH 9.0, virus yields were no greater than about 3 PFU/cell. Microscopic examination of the cells on the carriers indicated that the cells had lysed, but the virus was not released. The virus remained bound to the carriers, either directly through binding to their surface or indirectly by binding to the cellular components. Microscopic examination of stained carriers after treatment indicated that substantial cell debris remained on the carriers.

Trypsin treatment was investigated for extraction of the virus from bioreactor carriers that had undergone lysis by hypo osmotic shock (post-lysis carriers). Trial 1 compared the effects of the extraction medium, either PBS, Trypsin/EDTA (porcine trypsin), TrypLE (recombinant trypsin) or water. Additionally, the effects of freeze/thaw and sonication were evaluated. The results showed that each extraction method was successful, with the most effective extraction being obtained with TrypLE with added benefit from freeze/thaw alone or freeze/thaw and sonication. The virus extracted was 7.2 PFU/cell. With freeze/thaw and sonication, 3.3 PFU/cell were extracted in the PBS. Trial 2 repeated the comparison of TrypLE with and without freeze/thaw and sonication. The TrypLE with freeze/thaw and sonication extracted 7.0 PFU/cell.

Trial 3 compared Trypsin/EDTA, TrypLE, and 1 mm Tris pH 9.0 with and without freeze/thaw and sonication for extraction of bioreactor carriers without prior lysis (pre-lysis carriers). TrypLE with freeze/thaw and sonication extracted 9.1 PFU/cell.

The evaluation was repeated with carriers obtained from the bioreactor at 24, 48 and 72 hours post-infection (hpi) that had been frozen and thawed, but not previously lysed. Trial 4 compared the extraction of 72 hpi carriers with PBS, Trypsin/EDTA and TrypLE with and without freeze/thaw and sonication (FIG. 25). Trypsin/EDTA yielded 19 PFU/cell and TrypLE yielded 60 PFU/cell. All of these results were obtained with freeze/thaw and sonication of the carriers after the extraction. With only freeze/thaw, PBS yielded 2.7 PFU/cell, Trypsin/EDTA yielded 17.5 PFU/cell, and TrypLE yielded 40.4 PFU/cell. The carriers used in Trial 4 were extracted a second time using the same conditions. In this case, TrypLE, TrypLE with freeze/thaw, and TrypLE with freeze/thaw and sonication each extracted less than 1.3 PFU/cell.

Extraction of the carriers sampled at 48 hpi yielded less virus than the 72 hpi carriers. TrypLE alone, TrypLE with freeze/thaw, and TrypLE with freeze/thaw and sonication extracted 12.2, 25.1 and 22.1 PFU/cell, respectively. The carriers sampled at 24 hours extracted 13.7, 18.3 and 19.8 PFU/cell under the three methods, respectively.

Virus aliquots of known titer were incubated in TrypLE at either 21° C. or 37° C. for 5, 10, 15, 30, 45 or 60 minutes. There was no substantial reduction in viral titer at either temperature. If anything, the viral titer increased with incubation with TrypLE.

Example 4

Virus Infection, Amplification and Harvest

Increasing the contact of the reactor carriers with the harvest solution was accomplished by either increasing time or increasing volume.

Experiments 7, 8 and 9 were infected with GLV-1h68 in 600 mL of infection medium at MOI of 0.2 in order to achieve rapid and efficient infection of the cells. The amplification period was set at 72 hours for all three experiments. The result was achieved as evident by the rapid decline in cell density immediately after infection (FIG. 27). At 72 hours post-infection, the reactors were harvested by draining the medium and rinsing with PBS. The Experiment 7 bioreactor was harvested immediately. The bioreactors of Experiments 8 and 9 were frozen and processed later. TrypLE solution was added to the reactor in PBS and circulated by agitation. The harvest volume was collected and the reactor was rinsed with additional volumes. The harvest and rinse volumes were sampled and analyzed for virus content by VPA.

Experiment 7 was harvested with 300 mL of 1×TrypLE at 21° C. for 45 minutes, followed by 9 consecutive rinses with 300 or 500 mL of 10 mM Tris-HCL pH 9.0. The reactor was not frozen prior to harvest. Analysis of the virus content of the harvest and rinse fractions indicated that the virus was harvested from the bioreactor continuously throughout the process. The 3rd rinse fraction, with the maximum virus content, was only 16% of the total virus harvested. In fact, the last rinse fraction still had 4% of the total virus harvested. $1.3\times10^{10}$ pfu of GLV-1h68 was recovered.

TABLE 1

Virus Harvest of Nano Experiment 7

| Condition | Volume (mL) | Temp (° C.) | Duration (Min) | Total Virus in Sample (PFU) | % of Total Harvest |
|---|---|---|---|---|---|
| (1x) TrypLE | 300 | 21 | 45 | 9.8E+08 | 7% |
| 10 mM Tris-Cl pH 9.0 | 300 | 21 | 5 | 6.5E+08 | 5% |
| | 300 | 21 | 5 | 1.3E+09 | 10% |
| | 300 | 21 | 5 | 2.1E+09 | 16% |
| | 500 | 21 | 5 | 2.0E+09 | 15% |
| | 500 | 21 | 5 | 1.4E+09 | 11% |
| | 500 | 21 | 5 | 7.1E+08 | 5% |
| | 300 | 21 | 5 | 5.8E+08 | 4% |
| Total | 3000 | — | — | 1.3E+10 | |

Experiment 8 was harvested after freeze/thaw of the bioreactor. TrypLE (prepared by dilution of 10×TrypLE to 300 mL in PBS) at 21° C. for 45 minutes, followed by 10 consecutive rinses with 300 mL each of 10 mM Tris-HCL pH 9.0. The first 5 rinses were carried out with continuous maximum agitation and the final rinses used multiple intermittent burst agitations. Compared to Experiment 7, the 2nd rinse fraction had the maximum virus content, with 20% of the total virus harvested. Successive rinse fractions had appreciable virus and the last rinse fraction still had 5% of the total virus harvested. The total virus harvested was $1.7 \times 10^{10}$ pfu of GLV-1h68.

TABLE 2

Virus Harvest of Nano Experiment 8

| Condition | Volume (mL) | Temp (° C.) | Duration (Min) | Total Virus in Sample (PFU) | % of Total Harvest |
|---|---|---|---|---|---|
| 1x TrypLE (10x) | 310 | 21 | 45 | 1.4E+09 | 8% |
| 10 mM Tris-Cl pH 9.0 with Continuous Agitation | 300 | 21 | 5 | 2.2E+09 | 13% |
|  | 300 | 21 | 5 | 3.4E+09 | 20% |
|  | 300 | 21 | 5 | 2.4E+09 | 14% |
|  | 300 | 21 | 5 | 1.4E+09 | 8% |
| 10 mM Tris-Cl pH 9.0 with Disrupted Agitation | 300 | 21 | 5 | 1.5E+09 | 9% |
|  | 300 | 21 | 5 | 1.5E+09 | 9% |
|  | 300 | 21 | 5 | 1.2E+09 | 7% |
|  | 300 | 21 | 5 | 9.4E+08 | 6% |
| Every Minute | 300 | 21 | 5 | 8.6E+08 | 5% |
| Total | 3010 | — | — | 1.7E+10 |  |

In Experiment 9 harvesting occurred after freeze/thaw with 500 mL of TrypLE (prepared by dilution of 10×TrypLE in PBS) at 37° C. for 60 minutes, followed by 2 rinses with 500 mL each of 10 mM Tris-HCL pH 9.0, 2 rinses with PBS, and then lastly with 2 rinses with PBS containing 1 M NaCl. Maximum continuous agitation was used throughout. The 2nd rinse fraction with 10 mM Tris-HCl pH 9.0 again contained the maximum virus content; however the relative proportion of the total harvest was greater than previous harvests (32%). Additionally, the TrypLE harvest fraction and the 1st rinse contained significant fractions of the virus (27 and 29%, respectively). Subsequent rinses with PBS had diminishing virus content (9.4 and 1.9%), and the last rinses with PBS containing 1 M NaCl had significantly reduced virus content (0.5 and 0.2%). The total virus harvested from Experiment 9 was $7.3 \times 10^{10}$ PFU.

Reducing the total volume of virus harvest could facilitate downstream processing steps. Therefore, improving the efficiency of virus release at each step is advantageous.

Carriers were sampled from the bioreactor after harvest, extracted and tested by VPA. The carriers contained $4.9 \times 10^6$ PFU/carrier, which for the entire bioreactor at time of harvest containing 914 carriers indicated a residual post-harvest virus content of $4.5 \times 10^9$ PFU or 6% of the total virus harvested. Therefore, the recovery of virus during the harvest procedure was estimated to be at least 94%. There were $1.5 \times 10^9$ cells contained in the bioreactor at time of infection. Therefore, the specific virus productivity was $[7.3 \times 10^{10} + (7.3 \times 10^{10} \times 0.06)]$ PFU/$1.5 \times 10^9$ cells=52 PFU/cell.

TABLE 3

Virus Harvest of Nano Experiment 9

| Condition | Volume (mL) | Temp (° C.) | Duration (Min) | Total Virus in Sample (PFU) | % of Total Harvest |
|---|---|---|---|---|---|
| 1x TrypLE (10x) | 500 | 37 | 60 | 2.0E+10 | 27% |
| 10 mM Tris-Cl pH 9.0 | 500 | 37 | 5 | 2.2E+10 | 29% |
|  | 500 | 37 | 5 | 2.3E+10 | 32% |
| PBS | 500 | 37 | 5 | 6.9E+09 | 9.4% |
|  | 500 | 37 | 5 | 1.4E+09 | 1.9% |

TABLE 3-continued

Virus Harvest of Nano Experiment 9

| Condition | Volume (mL) | Temp (° C.) | Duration (Min) | Total Virus in Sample (PFU) | % of Total Harvest |
|---|---|---|---|---|---|
| 1M NaCl in PBS | 500 | 37 | 5 | 3.4E+08 | 0.5% |
|  | 500 | 37 | 5 | 1.4E+08 | 0.2% |
| Total | 3500 | — | — | 7.3E+10 |  |

Example 5

Purification of GLV-1h68 from the iCellis® Bioreactor harvest

Five bioreactor runs (Nano Experiments 7, 8, 9, 10 and 11) were used to evaluate the virus purification process using ultrafiltration in a tangential flow (i.e. cross flow) mode. The virus harvest of Nano Experiment 7 (3,500 mL in total) was frozen at −20° C. in aliquots. For each experiment, an aliquot of the virus harvest was thawed at 4° C. and/or at room temperature just prior to use. For other experiments, the virus harvest was purified directly by UF/DF without prior freezing.

Nano Experiment 8 Virus Harvest UF/DF Purified Using Centramate LV 300 Kilodaltons Cut-Off (Kdco) Filter The virus was harvested from the Nano Experiment 8 bioreactor in 3.5 L. Ultrafiltration was performed using a Centramate LV 300 kdco filter at an initial flow rate of 9.1 L/min/M² until the retentate volume was reduced to 900 mL. The retentate was stored at −20° C. overnight. UF was resumed until the retentate volume was reduced to 500 mL. Diafiltration was conducted by adding seven successive diavolumes of PBS. The final retentate and filter washes were combined for a total volume of 300 mL. The viral titer of samples was determined by VPA and the protein and DNA contents were determined by protein and DNA assays.

The results showed that virus recovery after ultrafiltration was 80% and after diafiltration was 36%. The protein content of the UF retentate was 21.3 mg/$10^9$ pfu and the DNA content was 455 μg/$10^9$ pfu. After diafiltration, the protein content of the DF retentate was reduced to 9.0 mg/$10^9$ pfu (2.4 fold reduction) and the DNA content was reduced to 17 μg/$10^9$ pfu (26 fold).

TABLE 4

Nano Experiment 8 virus harvest UF/DF purified using Centramate LV 300 kdco filter

| Fraction | Filtration Solution | Flow Rate (L/min/M²) | Fraction Volume (mL) | Fraction Virus (PFU) | Virus Recovery (%) |
|---|---|---|---|---|---|
| Starting Material | — | — | 3500 | 1.7E+10 | 100% |
| UF Permeate | PBS | 9.1 | 3000 | 6.3E+08 | 4% |
| UF Retentate | PBS | 9.1 | 500 | 1.4E+10 | 80% |
| DF Permeate | PBS | 9.1 | 4500 | 8.7E+06 | 0.0% |
| DF Retentate | PBS | 9.1 | 300 | 6.1E+09 | 36% |

TABLE 5

Protein and DNA analysis of Nano Experiment 8 virus harvest UF/DF purified using Centramate LV 300 kdco filter

| Test Sample | PFU Total | Protein (mg)/ 10E9 PFU | DNA (µg)/ 10E9 PFU | Specific Activity (pfu/mg protein) | Fold Change | Specific Activity (pfu/µg DNA) | Fold Change |
|---|---|---|---|---|---|---|---|
| UF Retentate | 1.2E+10 | 21.3 | 455 | 4.7E+07 | N/A | 2.2E+06 | N/A |
| DF Retentate | 6.1E+09 | 9.0 | 17 | 1.1E+08 | 2.4 | 5.7E+07 | 26 |

Nano Experiment 7 Virus Harvest Purified Using Centramate LV 300 Kdco Filter UF/DF An aliquot of the virus harvest of the Nano Experiment 7 bioreactor (1000 mL) was concentrated using the Centramate LV 300 kdco filter. The UF retentate (200 mL) was then diafiltered first against 10 diavolumes (2000 mL) of PBS followed by 10 diavolumes (2000 mL) of low ionic strength and high pH buffer (10 mM Tris-CL pH 9.0).

Virus recovery after initial concentration of the virus harvest from 1000 ml to 200 mL was 67%. After diafiltration against PBS, the virus recovery was 16%. After subsequent diafiltration against 10 mM Tris-CL, pH 9.0, the virus recovery returned to 81%.

TABLE 6

Nano Experiment 7 virus harvest UF/DF purified using Centramate LV 300 kdco filter

| Fraction | Filtration Solution | Flow Rate (L/min/M²) | Fraction Volume (mL) | Fraction Virus (PFU) | Virus Recovery (%) |
|---|---|---|---|---|---|
| Starting Material | — | — | 1000 | 5.5E+09 | 100% |
| UF Permeate | PBS | 4.4 | 800 | 3.8E+04 | 0.0% |
| UF Retentate | PBS | 4.4 | 200 | 3.7E+09 | 67% |
| DF Permeate | PBS | 4.4 | 2000 | ND[1] | 0.0% |
| DF Retentate | PBS | 4.4 | 200 | 9.0E+08 | 16% |
| DF Permeate | 10 mM Tris-Cl pH 9.0 | 4.4 | 2000 | ND[1] | 0.0% |
| DF Retentate | 10 mM Tris-Cl pH 9.0 | 4.4 | 200 | 4.5E+09 | 81% |

[1]None detected.

Nano Experiment 9 Virus Harvest Purified Using Centramate LV 300 Kdco Filter UF/DF The virus was harvested from the Nano Experiment 9 bioreactor in 3.5 L. Ultrafiltration was performed using a Centramate LV 300 kdco filter at an initial flow rate of 4.4 L/min/M² until the retentate volume was reduced to 200 mL. Diafiltration was conducted by adding five successive diavolumes of PBS (200 mL each) followed by adding five successive diavolumes of 10 mM Tris-CL, pH 9.0 (200 mL each). Samples of the UF and DF retentate and permeate fractions were tested for viral titer by VPA and protein and DNA contents by protein and DNA assays.

The results show that virus recovery in the retentate after ultrafiltration was 88% and after diafiltration against PBS was 67%. After diafiltration against 10 mM Tris-Cl, pH 9.0 the recovery in the retentate fraction was 107%. The protein content of the UF retentate was 1.3 mg/10⁹ pfu and the DNA content was 20 µg/10⁹ pfu. After diafiltration, the protein content of the DF retentate was reduced to 0.6 mg/10⁹ pfu (1.4 fold reduction) and the DNA content was reduced to 16 µg/10⁹ pfu (0.8 fold).

TABLE 7

Nano Experiment 9 virus harvest UF/DF purified using Centramate LV 300 kdco filter

| Fraction | Filtration Solution | Flow Rate (L/min/M²) | Fraction Volume (mL) | Fraction Virus (PFU) | Virus Recovery (%) |
|---|---|---|---|---|---|
| Starting Material | — | — | 3500 | 7.3E+10 | 100% |
| UF Permeate | PBS | 4.4 | 3300 | 6.0E+05 | 0.0% |
| UF Retentate | PBS | 4.4 | 200 | 6.5E+10 | 88% |
| DF Permeate | PBS | 4.4 | 1000 | 9.0E+04 | 0.0% |
| DF Retentate | PBS | 4.4 | 200 | 4.5E+10 | 67% |
| DF Permeate | 10 mM Tris-Cl pH 9.0 | 4.4 | 1000 | 8.8E+05 | 0.0% |
| DF Retentate | 10 mM Tris-Cl pH 9.0 | 4.4 | 200 | 7.8E+10 | 107% |

TABLE 8

Protein and DNA analysis of Nano Experiment 9 virus harvest UF/DF purified using Centramate LV 300 kdco filter

| Test Sample | PFU Total | Protein (mg)/ 10E9 PFU | DNA (µg)/ 10E9 PFU | Specific Activity (pfu/mg protein) | Fold Change | Specific Activity (pfu/µg DNA) | Fold Change |
|---|---|---|---|---|---|---|---|
| UF Retentate | 6.5E+10 | 0.9 | 13 | 1.1E+09 | N/A | 7.5E+07 | N/A |
| DF Retentate | 7.4E+10 | 0.6 | 16 | 1.6E+09 | 1.4 | 6.3E+07 | 0.8 |

Virus Harvest Purification by UF/DF Using MidiKros Hollow-Fiber Filter Cartridges.

The Centramate LV uses flat membrane filters. The MidiKros filters are cartridges assembled from hollow fibers with porosities of 500 kdco and 750 kdco. UF/DF purification of the virus harvest was evaluated with these filter cartridges to determine the effect of filter geometry and increased porosity. Aliquots of the virus harvest from Nano Experiment 7 stored at −20 C were thawed and used in UF/DF purification. The MidiKros 500 kdco hollow-fiber filter was used to concentrate 500 mL of the virus harvest to a volume of 100 mL, followed by diafiltration against 10 diavolumes of 10 mM Tris-Cl, pH 9.0 (CFF 12). Samples of the starting material, UF and DF permeate and retentate fractions were tested for titer by VPA and protein and DNA content. The results showed a virus recovery of 79% after UF and 68% after DF. No virus was detected in the permeate fractions either during UF or DF. Similarly, 500 mL of the virus harvest was purified by UF/DF using the MidiKros 750 kdco hollow-fiber filter (CFF 13). The virus recovery was 66% after UF and 43% after DF. The protein and DNA content of the starting material was 5.1 mg/10⁹ pfu and 400 µg/10⁹ pfu, respectively. After UF/DF, the protein and DNA content of the retentate of the MidiKros 500 kdco filter was 1.3 mg/10⁹ pfu and 90 µg/10⁹ pfu, respectively (4.0 and 4.5 fold reductions, respectively). After UF/DF, the protein and DNA content of the retentate of the MidiKros 750 kdco filter was 1.9 mg/10⁹ pfu and 63 µg/10⁹ pfu, respectively (2.7 and 6.4 fold reductions, respectively).

TABLE 9

Nano Experiment 7 virus harvest UF/DF purified using MidiKros 500 kdco hollow-fiber filter

| Fraction (CFF 12) | Filtration Solution | Flow Rate (L/Min/M$^2$) | Fraction Volume (mL) | Fraction Virus (PFU) | Virus Recovery (%) |
|---|---|---|---|---|---|
| Starting Material | — | — | 500 | 1.8E+09 | 100% |
| UF Permeate | PBS | 4.4 | 400 | ND[1] | 0.0% |
| UF Retentate | PBS | 4.4 | 100 | 1.4E+09 | 79% |
| DF Permeate | 1 mM Tris-Cl pH 9.0 | 4.4 | 1000 | ND[1] | 0.0% |
| DF Retentate | 1 mM Tris-Cl pH 9.0 | 4.4 | 73 | 1.2E+09 | 68% |

[1]None detected.

TABLE 10

Nano Experiment 7 virus harvest UF/DF purification using MidiKros 750 kdco hollow-fiber filter

| Fraction (CFF 13) | Filtration Solution | Flow Rate (L/Min/M$^2$) | Fraction Volume (mL) | Fraction Virus (PFU) | Virus Recovery (%) |
|---|---|---|---|---|---|
| Starting Material | — | — | 500 | 1.8E+09 | 100% |
| UF Permeate | PBS | 4.4 | 400 | ND[1] | 0.0% |
| UF Retentate | PBS | 4.4 | 100 | 1.2E+09 | 66% |
| DF Permeate | 1 mM Tris-Cl pH 9.0 | 4.4 | 1000 | ND[1] | 0.0% |
| DF Retentate | 1 mM Tris-Cl pH 9.0 | 4.4 | 73 | 7.6E+08 | 43% |

[1]None detected.

TABLE 11

Protein and DNA analysis of Nano Experiment 7 virus harvest UF/DF purification using MidiKros 500 kdco and 750 kdco hollow-fiber filter

| Test Sample | PFU Total | Protein (mg)/ 10E9 PFU | DNA (µg)/ 10E9 PFU | Specific Activity (pfu/mg protein) | Fold Change | Specific Activity (pfu/µg DNA) | Fold Change |
|---|---|---|---|---|---|---|---|
| CFF 12,13 Starting Material | 1.8E+09 | 5.1 | 402 | 2.0E+08 | N/A | 2.8E+06 | N/A |
| CFF 12 DF Retentate | 1.2E+09 | 1.3 | 90 | 7.9E+08 | 4.0 | 1.2E+07 | 4.5 |
| CFF 13 DF Retentate | 7.6E+08 | 1.9 | 63 | 5.4E+08 | 2.7 | 1.8E+07 | 6.4 |

Nano Experiment 10 Virus Harvest Purified by UF/DF Using MidiKros 750 kdco Hollow-Fiber Filter The virus harvest from Nano Experiment 10 was purified by UF/DF using a MidiKros 750 kdco hollow-fiber filter cartridge. 3.5 L of the virus harvest was concentrated by ultrafiltration to 200 mL followed by diafiltration against 10 diavolumes of 10 mM Tris-Cl, pH 9.0 (200 mL each). Samples of the permeate and retentate fractions were tested for virus titer by VPA and protein and DNA content. Virus recovery after UF concentration was 112% and after diafiltration was 97%. The protein content of the UF starting material was 4.0 mg/10$^9$ pfu and the DNA content was 166 µg/10$^9$ pfu. After diafiltration, the retentate was 1.0 mg/10$^9$ pfu (4 fold reduction over the starting material) and the DNA content was 15 µg/10$^9$ pfu (11.1 fold reduction over the starting material).

TABLE 12

Nano Experiment 10 virus harvest purified by UF/DF using MidiKros 750 kdco hollow-fiber filter

| Fraction | Filtration Solution | Flow Rate (L/min/M$^2$) | Fraction Volume (mL) | Fraction Virus (PFU) | Virus Recovery (%) |
|---|---|---|---|---|---|
| Starting Material | — | — | 3500 | 1.7E+11 | 100% |
| UF Permeate | PBS | 2.5 | 3300 | ND[1] | 0.0% |
| UF Retentate | PBS | 2.5 | 150 | 2.0E+11 | 112% |
| DF Permeate | 10 mM Tris-Cl pH 9.0 | 2.5 | 1000 | ND[1] | 0.0% |
| DF Retentate | 10 mM Tris-Cl pH 9.0 | 2.5 | 200 | 1.7E+11 | 97% |

[1]None detected.

TABLE 13

Protein and DNA analysis of Nano Experiment 10 virus harvest purified by UF/DF using MidiKros 750 kdco hollow-fiber filter

| Test Sample | PFU Total | Protein (mg)/ 10E9 PFU | DNA (µg)/ 10E9 PFU | Specific Activity (pfu/mg protein) | Fold Change | Specific Activity (pfu/µg DNA) | Fold Change |
|---|---|---|---|---|---|---|---|
| Nano 10 UF-SM | 1.7E+11 | 4.0 | 166 | 2.5E+08 | N/A | 6.0E+06 | N/A |
| Nano 10 DF Retentate | 1.7E+11 | 1.0 | 15 | 9.9E+08 | 4.0 | 6.7E+07 | 11.1 |

Nano Experiment 11 Virus Harvest Purified by UF/DF Using MidiKros 500 kdco Hollow-Fiber Filter The virus harvest from Nano Experiment 11 was purified by UF/DF using a MidiKros 500 kdco hollow-fiber filter cartridge. 2.5 L of the virus harvest was concentrated by ultrafiltration to 200 mL followed by diafiltration against 10 diavolumes of 10 mM Tris-Cl, pH 9.0 (200 mL each). Samples of the permeate and retentate fractions were tested for virus titer by VPA and protein and DNA content. Virus recovery after UF concentration was 147% and after diafiltration was 105%. The protein content of the UF starting material was 5.1 mg/10$^9$ pfu and the DNA content was 166 µg/10$^9$ pfu. After ultrafiltration concentration, the retentate was 1.1 mg/10$^9$ pfu (4.9 fold reduction over the starting material) and the DNA content was 22 µg/10$^9$ pfu (7.4 fold reduction over the starting material). After diafiltration, the retentate was 1.4 mg/10$^9$ pfu (3.8 fold reduction over the starting material) and the DNA content was 25 µg/10$^9$ pfu (6.5 fold reduction over the starting material).

TABLE 14

Nano Experiment 11 virus harvest purified by UF/DF using MidiKros 500 kdco hollow-fiber filter

| Condition | Filtration Solution | Flow Rate (L/min/M$^2$) | Fraction Volume (mL) | Fraction Virus (PFU) | Virus Recovery (%) |
|---|---|---|---|---|---|
| Starting Material | PBS | — | 2500 | 6.5E+10 | 100% |
| UF Permeate | PBS | 2.8 | 2300 | ND[1] | 0.0% |
| UF Retentate | PBS | 2.8 | 200 | 9.6E+10 | 147% |
| DF Permeate | 10 mM Tris-Cl pH 9.0 | 2.8 | 2000 | ND[1] | 0.0% |
| DF Retentate | 10 mM Tris-Cl pH 9.0 | 2.8 | 195 | 6.8E+10 | 105% |

[1]None detected.

TABLE 15

Protein and DNA analysis of Nano Experiment 11 virus harvest purified by UF/DF using MidiKros 500 kdco hollow-fiber filter

| Test Sample | PFU Total | Protein (mg)/ 10E9 PFU | DNA (μg)/ 10E9 PFU | Specific Activity (pfu/mg protein) | Fold Change | Specific Activity (pfu/μg DNA) | Fold Change |
|---|---|---|---|---|---|---|---|
| Nano 11 UF SM | 6.5E+10 | 5.1 | 166 | 1.9E+08 | N/A | 6.0E+06 | N/A |
| Nano 11 UF Retentate | 9.6E+10 | 1.1 | 22 | 9.5E+08 | 4.9 | 4.4E+07 | 7.4 |
| Nano 11 DF Retentate | 6.8E+10 | 1.4 | 25 | 7.4E+08 | 3.8 | 3.9E+07 | 6.5 |

Nano Experiment 12 Virus Harvest Purified by UF/DF Using MidiKros 500 kdco Hollow-Fiber Filter The virus was harvested from Nano Experiment 12 by thawing the frozen bioreactor by addition of 500 mL 10 mM Tris-HCl, 2 mM MgCl2, pH 9.0. Benzonase® (Recombinant Benzonase®, Speed BioSystems, Inc.) was added to 100 U/mL and incubated with agitation at 37° C. for 60 minutes. The Benzonase® nuclease digestion medium was removed and replaced with 500 mL of PBS containing 1×TrypLE and further incubated with agitation at 37° C. for 60 minutes. The TrypLE harvest medium was removed and the bioreactor was flushed twice with 500 mL of 10 mM Tris-HCl, pH 9.0 with agitation at 37° C. for 10 minutes each. The TrypLE harvest and both flush volumes were combined as the virus harvest (1.5 L). Viral titer analysis by VPA indicated that the TrypLE virus harvest fraction contained 80.1% of the virus, the first 10 mM Tris-HCl flush contained 16.3%, and the second flush contained 2.4%. Therefore, 98.8% of the virus was released from the bioreactor and collected in the virus harvest. The Benzonase® nuclease digestion fraction contained 0.4% of the virus and the macrocarriers after harvest contained less than 0.1%.

The virus harvest was purified by UF/DF using a MidiKros 500 kdco hollow-fiber filter cartridge. 1.5 L of the virus harvest was concentrated by ultrafiltration to 200 mL followed by diafiltration against 10 diavolumes of 10 mM Tris-Cl, pH 9.0 (200 mL each). Samples of the permeate and retentate fractions were tested for virus titer by VPA and protein and DNA content. Virus recovery after UF concentration was 45% and after diafiltration was 123%. The protein content of the UF starting material was 4.3 mg/10$^9$ pfu and the DNA content was 38 μg/10$^9$ pfu. After ultrafiltration concentration, the retentate was 4.0 mg/10$^9$ pfu (1.1 fold reduction over the starting material) and the DNA content was 5 μg/10$^9$ pfu (8.7 fold reduction over the starting material). After diafiltration, the retentate was 1.6 mg/10$^9$ pfu (2.7 fold reduction over the starting material) and the DNA content was 1 μg/10$^9$ pfu (42 fold reduction over the starting material).

TABLE 16

Nano Experiment 12 virus harvest purified by UF/DF using MidiKros 500 kdco hollow-fiber filter

| Condition | Filtration Solution | Flow Rate (L/min/M$^2$) | Fraction Volume (mL) | Fraction Virus (PFU) | Virus Recovery (%) |
|---|---|---|---|---|---|
| Starting Material | PBS | — | 1500 | 5.3E+10 | N/A |
| UF Permeate | PBS | 2.8 | 1300 | ND[1] | 0.0% |
| UF Retentate | PBS | 2.8 | 200 | 2.4E+10 | 45% |
| DF Permeate | 10 mM Tris-Cl pH 9.0 | 2.8 | 2000 | ND[1] | 0.0% |
| DF Retentate | 10 mM Tris-Cl pH 9.0 | 2.8 | 255.5 | 6.5E+10 | 123% |

[1]None detected.

TABLE 17

Protein and DNA analysis of Nano Experiment 12 virus harvest purified by UF/DF using MidiKros 500 kdco hollow-fiber filter

| Test Sample | PFU Total | Protein (mg)/ 10E9 PFU | DNA ((M$_9$) μg)/ 10E9 PFU | Specific Activity (pfu/mg protein) | Fold Change | Specific Activity (pfu/μg DNA) | Fold Change |
|---|---|---|---|---|---|---|---|
| Nano 12 UF SM | 5.3E+10 | 4.3 | 38 | 2.3E+08 | N/A | 2.6E+07 | N/A |
| Nano 12 UF Retentate | 2.4E+10 | 4.0 | 5 | 2.5E+08 | 1.1 | 2.1E+08 | 8.1 |
| Nano 12 DF Retentate | 6.5E+10 | 1.6 | 1 | 6.3E+08 | 2.7 | 1.1E+09 | 42 |

Example 6

Comparison with Prior Art Processes

The virus was produced by several processes employed in the art, and the results compared. One process referred to as the "CEF" process is the production of a virus from primary cells obtained from chicken eggs, grown in suspension culture, and infected with the virus. The cells are harvested by centrifugation, lysed by homogenization, purified by filtration, followed by two sucrose gradient centrifugations, followed by formulation and fill/finish.

"Process A" is the production of a virus in a continuous cell line, CV-1, grown in roller bottles (adherent culture), infected with the virus, the cells dissociated from the substrate with trypsin and collected by centrifugation. The cells are lysed by freeze thaw and the virus purified from the total cell lysate by affinity chromatography, followed by concentration by centrifugation, resuspension in formulation buffer and fill/finish.

"Process B," is a process as described herein. CV-1 cells are grown in a fixed-bed bioreactor (adherent culture), infected with the virus, the reactor drained of medium and frozen. The lysed adherent cells in the bioreactor are treated with Benzonase® nuclease followed by trypsin to release the virus, leaving the cell debris adhered to the matrix in the bioreactor. The virus is purified and formulated ultrafiltration and diafiltration, and filled/finished.

The tables below provide step-by-step comparisons of the various prior art processes, and the process herein (referred to a "Process B"). The process provided herein requires far fewer steps, and results in higher yield of virus.

TABLE 18

| GL-ONC1: CEF Process | Process A: CV-1 Roller Bottle/Chromatography Process | Process B: CV-1 iCellis/UF/DF Process |
| --- | --- | --- |
| SPF hen eggs incubation for 10-13 days | CV-1 cells | CV-1 cells |
| Extraction and Trypsinization of embryos and fractionation of CEF cells | CV-1 Cell Expansion | CV-1 Cell Expansion |
| CEF cell expansion and harvest | CV-1 Production Seeding/Growth | CV-1 Production Seeding/Growth |
| GL-ONC1 Infection/Amplification | GL-ONC1 A Infection/Amplification | GL-ONC1 B Infection/Amplification |
| Cell Harvest Centrifugation Resuspend, Homogenize, Ultrasonication Benzonase Treatment | Cell Harvest Centrifugation Virus Harvest/TrypLE/Tryp Inhibitor/Benzonase Treatments | Virus Harvest/TrypLE |
| Clarification/Centrifugation | Filtration (1.2 um) | UF/DF Final Formulation |
| High speed Centrifugation/Sucrose Resuspend, Homogenize, Ultrasonication | Adsorption Chromatography | |
| High speed Centrifugation/Sucrose Resuspend, Homogenize, Ultrasonication Final Formulation | Centrifugation Final Formulation | |
| Fill/Cap/Seal/Label | Fill/Cap/Seal/Label | Fill/Cap/Seal/Label |

TABLE 19

| Compares steps following lysis in the instant processes to the prior art process A | | | |
| --- | --- | --- | --- |
| 30 Roller Bottle (25,500 cm²) process A | | 11,000 cm² iCellis ® Nano process B | |
| Tryp. Inhibitor addition | Same volume as TrypLE = 19.5 mL | Treat with trypsin and optionally nuclease | |
| Typ. Inhib. incubation | 10 min, RT | | |
| MgCl2 addition | 2.5 mM final conc., add 2.9 mL of 200 mM | | |
| Benzonase ® nuclease | 75 U/mL final conc. | | |
| Incubate in nuclease | 6-15 hrs, RT | | |
| Filtration | 1.2 μm Sartopure ® filter (2); 10-100 mL/min Filter rinse | | |
| Freeze filtrate | −80 C. | | |
| Prepare HepSeph Column for use | Resin prep, column sanitization/pour column/prime and run | Ultrafiltration | 300 kdco Centramate T-series filter (1) 200 mL |
| Thaw virus suspension | RT | Diafiltration | 5 diavolumes of PBS 5 diavolumes of 10 mM Tris-HCl pH 9 200 mL |
| NaCl, sucrose addition | 100 mM NaCl, 2% sucrose | Diafiltration | 5 diavolumes of Final formulation buffer 200 mL |
| Equilibrate column | 5-8 mL/min | | |
| Load virus | 2-4 mL/min | | |
| Wash column | 5-8 mL/min | | |
| Elute virus | 5-8 mL/min | | |
| Centrifugation | 5300xg, 15-18 hr, 4 C. | | |
| Resuspend virus pellets | 100 mL Final formulation buffer | | |
| Fill/Label | Vial, cap/seal, label | Fill/Label | Via, cap/seal, label |

TABLE 20

Shows the higher yield from the instant process

| | 30 Roller Bottle (25,500 cm$^2$) Process A | 11,000 cm$^2$ iCellis ® Nano Process B | |
|---|---|---|---|
| | Values | Values | Difference B vs A |
| Name of Product | Toxbatch GL-ONC1 (Process A) | GLV-1h68 Nano Exp 9 DF-R10 (Process B) | N/A |
| Date of manufacture | Dec. 5, 2012 | Dec. 22, 2014 | N/A |
| Strength/Potency | $5.4 \times 10^7$ pfu/mL | $3.8 \times 10^8$ pfu/mL | N/A |
| Batch Size (mL) | 505 mL | 200 mL | N/A |
| Batch (pfu) | $2.7 \times 10^{10}$ pfu | $7.6 \times 10^{10}$ pfu | 2.8-Fold Increase |
| Specific Productivity (pfu/cm$^2$) | $1.1 \times 10^8$ pfu/cm$^2$ | $6.9 \times 10^6$ pfu/cm$^2$ | 6.5-Fold Increase |
| Batch Size (vials) | 459 vials | Not vialed | N/A |
| Vial content (mL) | 1.1 mL | N/A | N/A |
| Assay | | | |
| Titer | $5.4 \times 10^7$ pfu/mL | $3.8 \times 10^8$ pfu/mL | 7-Fold Increase |
| Total Protein Content | 1.01 mg/mL | 0.23 mg/mL | N/A |
| Total DNA Content | 669 ng/mL | 5,800 ng/mL | N/A |
| Specific Prot./$10^9$ pfu | 18.7 mg | 0.6 mg | 31-Fold Decrease |
| Specific DNA/$10^9$ pfu | 12.9 μg | 14.9 μg | Comparable |

Example 7

Exemplary large-scale process for producing vaccinia virus in a bioreactor, such as the 333 m$^2$ iCellis® 500 Bioreactor by the methods herein.

TABLE 21

| Overview manufacturing process GL-ONC1B | Scale/materials for 333 m$^2$ iCellis ® Bioreactor |
|---|---|
| CV-1 cells | MCB/WCB (1 vial): $1 \times 10^7$ cells |
| Cell expansion → T-Flask, Hyperstacks, or other suitable vessel | iCellis ® 333 m2: $1.5 \times 10^{10}$ cells |
| | Media volume: 64 L |
| production culture, seeding density $4.5 \times 10^3$ cells/cm$^2$ | Total Media: 350 L |
| Culture medium: DMEM high glucose/10% FBS | |
| 3-4 complete medium changes | |
| Infection with virus stock | Infection medium: 56 L |
| DMEM/FBS (2%), MOI 0.002 | Total cells at infection: $5.0 \times 10^{11}$ cells |
| Infection cell density: $1.5 \times 10^5$ cells/cm$^2$ | Virus stock: $1 \times 10^9$ pfu |
| Virus amplification 96 hr | |
| Freeze/Thaw | Thawing medium: 56 L, 10 mM Tris pH 9.0 |
| Remove all liquids, freeze at –70° C., 8-10 hours | |
| Thaw in 10 mM Tris pH 9.0, 37° C. | |
| Virus Harvest | Benzonase Vol: 56 L |
| Optional Benzonase treatment in 10 mM Tris pH 9.0, | Benzonase: $5 \times 10^6$ $U$ |
| 100 U/ml, 3 mM MgCl$_2$, 37° C., 30 min | Volume of TrypLE harvest: 56 L |
| Virus harvest TrypLE in PBS | TrypLE (10X): 5.6 L |
| 1x TrypLE, 37° C., 30 min | 10 mM Tris pH 9.0 washes: $3 \times 56$ L |
| Harvest washes in 10 mM Tris pH 9.0 (3 harvest volumes) | Virus Harvest Vol: 224 L |
| Ultrafiltration (25x concentration) | Starting material Vol: 224 L |
| Filtration device: 750 Kd M.W. cut-off, mPES, Filter 100 cm$^2$/L. | UF Concentrate Vol: 10 L |
| Diafiltration | |
| DF1: Buffer Exchange (10 DV of 10 mM Tris-HCl pH 9.0) | Volume of DF Retentate: 10 L |
| | DF1: 100 L |
| DF2: Buffer Exchange (5 DV of 10 mM Tris-HCl pH 7.8, 140 mM NaCl, 2% sucrose) | DF2: 50 L |
| Final Ultrafiltration Bulk Drug Substance (5-10×0 concentration) | Final Concentrate (BDS): 1-2 L Store frozen at –70° C. |

Since modifications will be apparent to those of skill in this art, it is intended that this invention be limited only by the scope of the appended claims.

What is claimed is:

1. A method for producing a virus, comprising:
 a) culturing host cells, comprising a virus, in a bioreactor, wherein the bioreactor comprises a matrix for growing adherent cells, wherein:
 the matrix is biocompatible and is of a density that entraps cells or is one to which cells adhere, whereby the cells are entrapped in and/or adhere to the matrix; and the density of the matrix is such that the cells remain entrapped and/or the matrix is one to which cells remain attached under conditions in which cells are lysed and treated to release the virus, and the flow of process culture medium through the matrix is sufficient for cell growth;

b) treating the cells that are entrapped in and/or adhered to the matrix to lyse them and release the virus into the process medium in the bioreactor, wherein the lysed cells remain adhered to and/or entrapped in the matrix; and then c) without further treatment of the process medium to remove cells or cell debris, and in only one or two steps, purifying the released virus from the process medium, wherein:

one step is ultrafiltration or diafiltration; and two steps are ultrafiltration and diafiltration.

2. The method of claim 1, wherein the host cells are adherent cells.

3. The method of claim 1, wherein the medium in the bioreactor is harvested prior to purifying the virus; and, optionally stored.

4. The method of claim 1, wherein purification, step c), of the virus is effected in 1 day or less.

5. The method of claim 1, consisting essentially of steps a), b) and c).

6. The method of claim 1, consisting of steps a), b) and c).

7. The method of claim 1, consisting essentially of steps a), b), c), wherein lysis step b) includes treating with protease and/or nuclease to release the virus from the entrapped and/or adhered cells.

8. The method of claim 1, consisting of steps a), b), c), wherein lysis step b) includes treating with protease and/or nuclease to release the virus from the entrapped and/or adhered cells.

9. The method of claim 1, wherein the cells are a cell line.

10. The method of claim 2, wherein the adherent cells are a cell line.

11. The method of claim 1, wherein the virus is a therapeutic virus.

12. The method of claim 1, wherein the virus is an enveloped virus.

13. The method of claim 1, wherein the virus is selected from among a Newcastle Disease virus, parvovirus, vaccinia virus, myxoma virus, measles virus, reovirus, vesicular stomatitis virus (VSV), adenovirus, adeno-associated virus, poliovirus, herpes virus, Sindbis virus and Seneca Valley virus, and derivatives thereof modified to contain a nucleic acid encoding a heterologous gene product.

14. The method of claim 1, wherein the virus is an oncolytic virus.

15. The method of claim 14, wherein the oncolytic virus is a vaccinia virus.

16. The method of claim 15, wherein the oncolytic vaccinia virus is selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, JX-594, Modified Vaccinia Ankara (MVA), Dairen I, LC16m8, LC16M0, LIVP, ACAM2000, WR 65-16, Connaught, New York City Board of Health (NYCBH), EM-63, and NYVAC strains.

17. The method of claim 15, wherein the vaccinia virus is a Lister strain virus.

18. The method of claim 17, wherein the vaccinia virus is an LIVP virus or a clonal strain of an LIVP virus.

19. The method of claim 18, wherein the virus is the LIVP virus designated GLV-1h68.

20. The method of claim 1, wherein the virus is a modified form containing a nucleic acid encoding a heterologous gene product.

21. The method of claim 20, wherein the heterologous gene product is a therapeutic or reporter gene product.

22. The method of claim 1, wherein the cells are mammalian cells.

23. The method of claim 22, wherein the mammalian cells are CV-1 cells.

24. The method of claim 22, wherein the mammalian cells are Vero cells.

25. The method of claim 22, wherein the mammalian cells are human cells.

26. The method of claim 22, wherein the mammalian cells are human fibroblast cells.

27. The method of claim 22, wherein the mammalian cells are human epithelial cells.

28. The method of claim 22, wherein the mammalian cells are human endothelial cells.

29. The method of claim 1, wherein the bioreactor contains a matrix or surface onto which adherent cells attach.

30. The method of claim 29, wherein the matrix in the bioreactor contains a non-fixed attachment surface.

31. The method of claim 30, wherein the surface is microcarrier beads, fibers, or woven mesh in suspension.

32. The method of claim 29, wherein the bioreactor contains a fixed attachment surface.

33. The method of claim 32, wherein the bioreactor is a packed bed bioreactor.

34. The method of claim 1, wherein lysing the cells and releasing the virus comprises exposing the bioreactor to freeze/thaw.

35. The method of claim 1, wherein lysing the cells and releasing the virus comprises exposing the cells to hypotonic medium.

36. The method of claim 1, wherein lysing the cells and releasing the virus comprises exposing the cells to detergent.

37. The method of claim 1, wherein lysing the cells and releasing the virus comprises exposing the cells to an enzyme.

38. The method of claim 37, wherein the enzyme is a protease.

39. The method of claim 37, wherein the enzyme is a nuclease.

40. The method of claim 37, wherein lysing the cells and releasing the virus comprises exposing the cells to a nuclease and a protease either sequentially or in combination.

41. The method of claim 1, wherein ultrafiltration employs a membrane having a nominal molecular weight cut off of between 300 and 750 kilodaltons or a nominal porosity of between 0.05 and 0.2 μm.

42. The method of claim 1, wherein ultrafiltration employs a membrane comprising polyethersulfone.

43. The method of claim 1, wherein ultrafiltration employs a flat membrane.

44. The method of claim 1, wherein ultrafiltration employs a hollow fiber membrane.

45. The method of claim 1, wherein ultrafiltration is performed in a tangential flow mode.

46. The method of claim 1, wherein ultrafiltration is performed in a cross flow mode.

47. The method of claim 1, wherein ultrafiltration is followed by diafiltration.

48. The method of claim 1, wherein the processed released virus is biologically active.

49. The method of claim 1, wherein the recovery of the processed released virus is greater than 50%.

* * * * *

UNITED STATES PATENT AND TRADEMARK OFFICE
CERTIFICATE OF CORRECTION

PATENT NO. : 10,851,350 B1  
APPLICATION NO. : 16/020850  
DATED : December 1, 2020  
INVENTOR(S) : Cappello et al.

Page 1 of 1

It is certified that error appears in the above-identified patent and that said Letters Patent is hereby corrected as shown below:

On the Title Page

The first or sole Notice should read --

Subject to any disclaimer, the term of this patent is extended or adjusted under 35 U.S.C. 154(b) by 36 days.

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*